US012680951B2

(12) United States Patent
Jayakumar et al.

(10) Patent No.: US 12,680,951 B2
(45) Date of Patent: Jul. 14, 2026

(54) SYSTEM, METHOD, AND COMPUTER PROGRAM PRODUCT FOR UTILIZING A FIBER BRAGG GRATING TO DETECT A GAS INDICATING THE ONSET OF THERMAL RUNAWAY

(71) Applicant: HONEYWELL INTERNATIONAL INC., Charlotte, NC (US)

(72) Inventors: Prince Ashwin Kumar Anburaj Jayakumar, Charlotte, NC (US); Nirmal A Kumar, Charlotte, NC (US); Shridhara Shanbhogue, Charlotte, NC (US); M Kantha Raj Urs, Charlotte, NC (US)

(73) Assignee: Honeywell International Inc., Charlotte, NC (US)

( * ) Notice: Subject to any disclaimer, the term of this patent is extended or adjusted under 35 U.S.C. 154(b) by 177 days.

(21) Appl. No.: 18/584,024

(22) Filed: Feb. 22, 2024

(65) Prior Publication Data

US 2024/0288364 A1 Aug. 29, 2024

(30) Foreign Application Priority Data

Feb. 27, 2023 (IN) .............................. 202311013200

(51) Int. Cl.
*G01N 21/3518* (2014.01)
*G01N 33/00* (2006.01)
(Continued)

(52) U.S. Cl.
CPC ..... *G01N 21/3518* (2013.01); *G01N 33/0047* (2013.01); *G02B 6/0208* (2013.01); *H01M 10/48* (2013.01); *G01N 2201/088* (2013.01)

(58) Field of Classification Search
CPC ........... G01N 21/3518; G01N 33/0047; G01N 2201/088; G02B 6/0208; H01M 10/48
See application file for complete search history.

(56) References Cited

U.S. PATENT DOCUMENTS 8,092,081 B2 1/2012 Hermann et al.
9,553,465 B2 * 1/2017 Raghavan .......... G01N 21/7703
(Continued)

FOREIGN PATENT DOCUMENTS

CN 2695957 Y 4/2005
CN 105987885 A * 1/2016 ............. G01N 21/01
(Continued)

OTHER PUBLICATIONS

Extended European Search Report Mailed on Jul. 2, 2024 for EP Application No. 24158095, 12 page(s).
(Continued)

*Primary Examiner* — Uzma Alam
*Assistant Examiner* — Fani Polyzos Boosalis
(74) *Attorney, Agent, or Firm* — Alston & Bird LLP

(57) ABSTRACT

An example system, method, and computer program product for detecting thermal runaway in a battery cell is provided. The example system includes a light source configured to emit light across a spectrum of wavelengths toward a sensing fiber having a first end and a second end. The sensing fiber may be positioned to receive the light emitted by the light source at the first end. The sensing fiber may further contain a filtering mechanism configured to reflect a portion of the spectrum of wavelengths of the light. In addition, the sensing fiber may be optically coupled to a photodiode at the second end, such that a portion of the light is reflected as the light travels through the sensing fiber. The gas may be detected based at least in part on an intensity of the light received at the photodiode indicating the onset of thermal runaway.

20 Claims, 11 Drawing Sheets

(51) Int. Cl.
  G02B 6/02 (2006.01)
  H01M 10/48 (2006.01)

(56) References Cited

U.S. PATENT DOCUMENTS

| | | | |
|---|---|---|---|
| 11,340,308 B1 | 5/2022 | Schreiber et al. | |
| 11,486,841 B2 | 11/2022 | Glenn et al. | |
| 2014/0092375 A1 | 4/2014 | Raghavan et al. | |
| 2017/0097464 A1* | 4/2017 | Challener | G02B 6/02366 |
| 2022/0412777 A1 | 12/2022 | Tong et al. | |

FOREIGN PATENT DOCUMENTS

| | | |
|---|---|---|
| CN | 113013514 A | 6/2021 |
| KR | 10-2022-0156306 A | 11/2022 |
| WO | 2011/072989 A1 | 6/2011 |
| WO | WO-2021209961 A1 * | 10/2021 ............. G01K 11/32 |

OTHER PUBLICATIONS

Mukund Kulkarni et al., "Development of Sensor and Optimal Placement for Smoke Detection in an Electric Vehicle Battery Pack," 2015 IEEE International Transportation Electrification Conference (ITEC), Aug. 27-29, 2015. [Retrieved from the Internet Sep. 26, 2024: URL: <https://ieeexplore.ieee.org/abstract/document/7386868>].

Yang-Duan Su et al., "Fiber Optic Sensing Technologies for Battery Management Systems and Energy Storage Applications," Sensors, 21(1397):1-34, (Feb. 17, 2021). [Retrieved from the Internet Jul. 25, 2024: URL: <https://www.mdpi.com/1424-8220/21/4/1397/htm>].

EP Office Action Mailed on Mar. 17, 2026 for EP Application No. 24158095, 7 page(s).

* cited by examiner

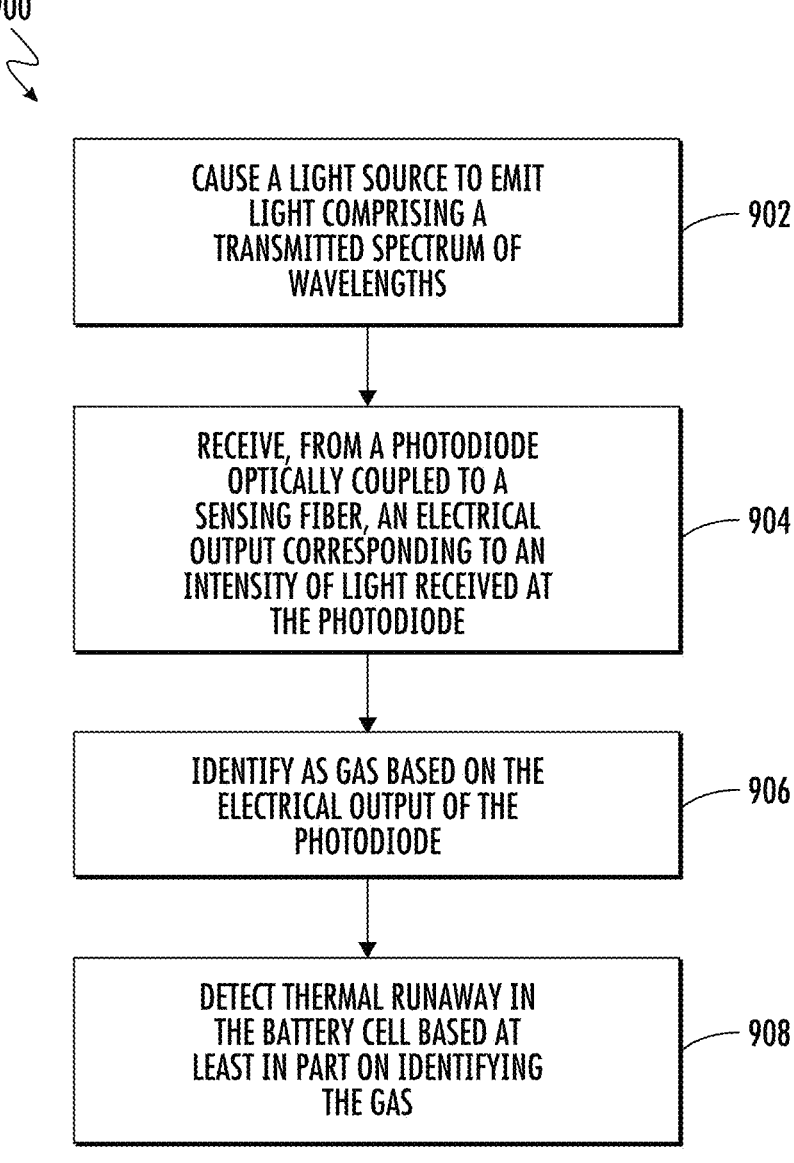

900

CAUSE A LIGHT SOURCE TO EMIT LIGHT COMPRISING A TRANSMITTED SPECTRUM OF WAVELENGTHS — 902

RECEIVE, FROM A PHOTODIODE OPTICALLY COUPLED TO A SENSING FIBER, AN ELECTRICAL OUTPUT CORRESPONDING TO AN INTENSITY OF LIGHT RECEIVED AT THE PHOTODIODE — 904

IDENTIFY AS GAS BASED ON THE ELECTRICAL OUTPUT OF THE PHOTODIODE — 906

DETECT THERMAL RUNAWAY IN THE BATTERY CELL BASED AT LEAST IN PART ON IDENTIFYING THE GAS — 908

FIG. 9

SYSTEM, METHOD, AND COMPUTER PROGRAM PRODUCT FOR UTILIZING A FIBER BRAGG GRATING TO DETECT A GAS INDICATING THE ONSET OF THERMAL RUNAWAY

CROSS-REFERENCE TO RELATED APPLICATIONS

This application claims priority pursuant to 35 U.S.C. 119(a) to Indian Application No. 202311013200, filed Feb. 27, 2023, which application is incorporated herein by reference in its entirety.

TECHNOLOGICAL FIELD

Embodiments of the present disclosure relate generally to systems for detecting gases, and more particularly, to systems for detecting gases released in the early stages of battery decay prior to the onset of thermal runaway.

BACKGROUND

Applicant has identified many technical challenges and difficulties associated with detecting the onset of thermal runaway in its early stages. Through applied effort, ingenuity, and innovation, Applicant has solved problems related to detecting gases released prior to the onset of thermal runaway by developing solutions embodied in the present disclosure, which are described in detail below.

BRIEF SUMMARY

Various embodiments are directed to an example system, method, and computer program product for detecting a gas indicative of the onset of thermal runaway.

In accordance with some embodiments of the present disclosure, an example system for detecting a gas is provided. The example system may comprise a light source configured to emit light comprising a spectrum of wavelengths and a sensing fiber comprising a first end and a second end. In some embodiments, the sensing fiber may be positioned to receive the light emitted by the light source at the first end. Further, in some embodiments, the sensing fiber may be optically coupled to a photodiode at the second end. In some embodiments, the sensing fiber may comprise a filtering mechanism configured to reflect a portion of the spectrum of wavelengths of the light. In addition, the gas may be detected based at least in part on an intensity of the light received at the photodiode.

In some embodiments, the filtering mechanism may be a fiber Bragg grating configured to reflect a reflected wavelength of the spectrum of wavelengths.

In some embodiments, the sensing fiber may comprise a plurality of filtering mechanisms wherein each of the plurality of filtering mechanisms is configured to reflect a different portion of the spectrum of wavelengths.

In some embodiments, the system may further comprise a plurality of sensing fibers each sensing fiber optically coupled to a receiving photodiode, wherein the filtering mechanism of each of the plurality of sensing fibers is configured to reflect a different portion of the spectrum of wavelengths.

In some embodiments, the gas may impede a transmittance of the light within the transmitted spectrum of wavelengths according to a spectral signature. In such an embodiment, the plurality of sensing fibers may be configured to identify the gas according to the spectral signature of the gas.

In some embodiments, the light source may comprise an array of light emitting diodes.

In some embodiments, the spectrum of wavelengths may comprise light of wavelengths between 0.75 micrometers and 15 micrometers.

In some embodiments, the gas may comprise at least one of ethylene carbonate, diethyl carbonate, dimethyl carbonate, and ethyl methyl carbonate.

In some embodiments, the system may further comprise a battery cell, wherein the light source and sensing fiber are positioned proximate the battery cell.

In some embodiments, detecting the gas may be an indicator of a first venting previous to an onset of thermal runaway in the battery cell.

In some embodiments, the system may further comprise a processor electrically connected to the light source and the photodiode, wherein the processor is configured to determine a presence of the gas based on an electrical output of the photodiode.

In some embodiments, the processor may utilize machine learning techniques to detect the gas based on the output of the photodiode.

In some embodiments, the processor may further receive physical environment information from one or more sensing devices and alter at least one detection parameter based on the physical environment information.

An example method for detecting thermal runaway in a battery cell is also provided. The example method may comprise causing a light source to emit light comprising a transmitted spectrum of wavelengths. The method may further comprise receiving, from a photodiode optically coupled to a sensing fiber, an electrical output corresponding to an intensity of light received at the photodiode. In some embodiments, the sensing fiber may comprise a first end and a second end, and the sensing fiber may be positioned to receive the light emitted by the light source at the first end. The sensing fiber may further be optically coupled to the photodiode at the second end. In addition, the sensing fiber may comprise a filtering mechanism configured to reflect a portion of the transmitted spectrum of wavelengths of the light. The method may further comprise identifying a gas based on the electrical output of the photodiode, and detecting thermal runaway in the battery cell based at least in part on identifying the gas.

In some embodiments, the method may further comprise utilizing machine learning techniques to identify the gas based on the electrical output of the photodiode.

In some embodiments, the method may further comprise utilizing a plurality of sensing fibers each sensing fiber optically coupled to a receiving photodiode to the gas, wherein the filtering mechanism of each of the plurality of sensing fibers is configured to reflect a different portion of the transmitted spectrum of wavelengths.

In some embodiments, the gas may impede a transmittance of the light within the transmitted spectrum of wavelengths according to a spectral signature, and the plurality of sensing fibers may be configured to identify the gas according to the spectral signature of the gas.

In some embodiments, the method may further comprise receiving physical environment information from one or more sensing devices, and altering at least one detection parameter based on the physical environment information.

In some embodiments, the transmitted spectrum of wavelengths may comprise light of wavelengths between 0.75 micrometers and 15 micrometers.

An example computer program product for detecting thermal runaway in a battery cell is also provided. In some embodiments, the computer program product may comprise at least one non-transitory computer-readable storage medium having computer-readable program code portions stored therein. In some embodiments, the computer-readable program code portions may comprise an executable portion configured to cause a light source to emit light comprising a transmitted spectrum of wavelengths. The executable portion may further be configured to receive, from a photodiode optically coupled to a sensing fiber, an electrical output corresponding to an intensity of light received at the photodiode. The executable portion may additionally be configured to identify a gas based on the electrical output of the photodiode, and detect thermal runaway in the battery cell based at least in part on identifying the gas. In some embodiments, the sensing fiber may comprise a first end and a second end, wherein the sensing fiber is positioned to receive the light emitted by the light source at the first end, and wherein the sensing fiber is optically coupled to the photodiode at the second end. In some embodiments, the sensing fiber may comprise a filtering mechanism configured to reflect a portion of the transmitted spectrum of wavelengths of the light.

BRIEF DESCRIPTION OF THE DRAWINGS

Reference will now be made to the accompanying drawings. The components illustrated in the figures may or may not be present in certain embodiments described herein. Some embodiments may include fewer (or more) components than those shown in the figures in accordance with an example embodiment of the present disclosure.

FIG. 9 depicts an example flowchart of an example method for detecting thermal runaway in a battery cell in accordance with an example embodiment of the present disclosure.

DETAILED DESCRIPTION

Figure 1:
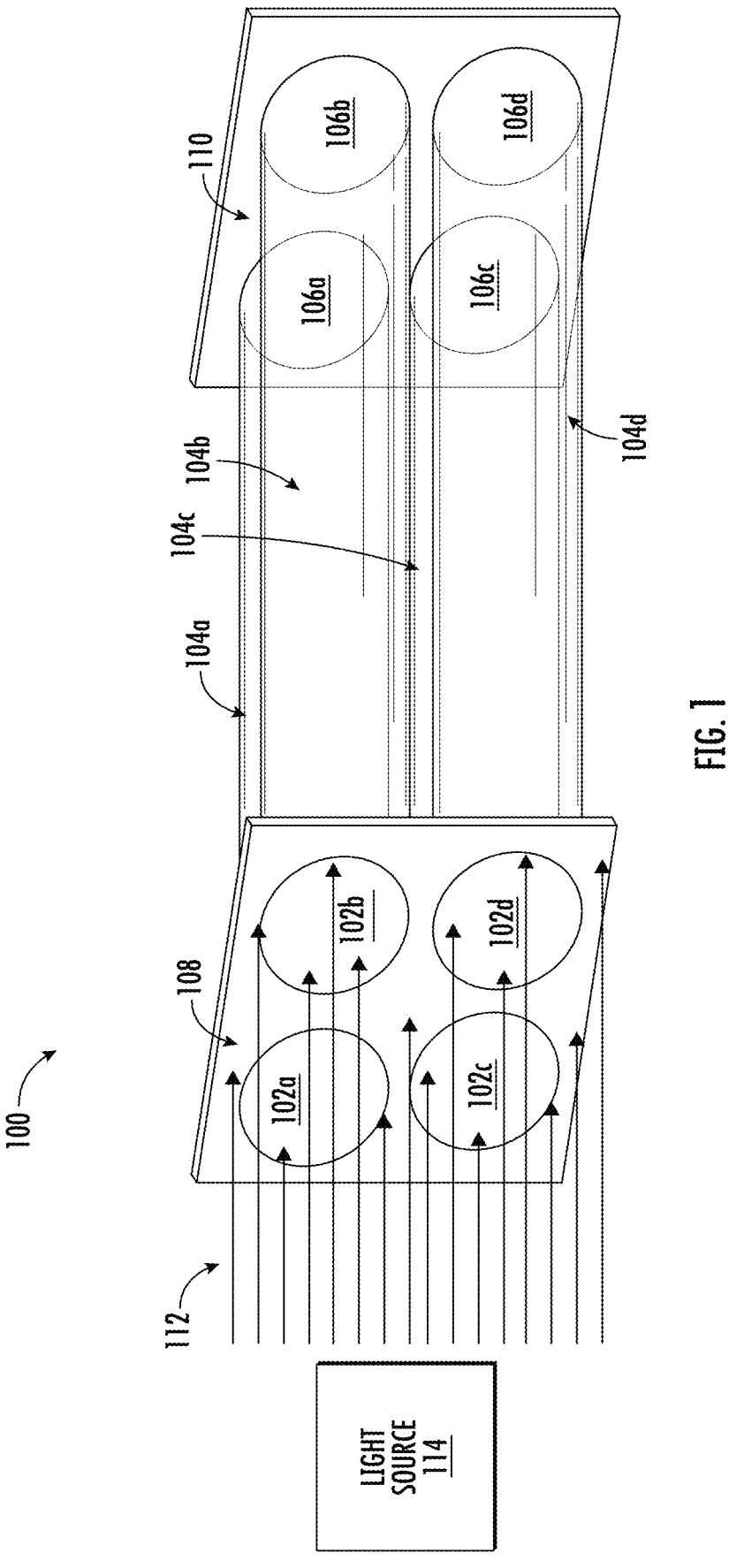
FIG. 1 illustrates a diagram of an example emitted light receiver of an example thermal runaway detection system in accordance with an example embodiment of the present disclosure.

Example embodiments will be described more fully hereinafter with reference to the accompanying drawings, in which some, but not all embodiments of the inventions of the disclosure are shown. Indeed, embodiments of the disclosure may be embodied in many different forms and should not be construed as limited to the embodiments set forth herein; rather, these embodiments are provided so that this disclosure will satisfy applicable legal requirements. Like numbers refer to like elements throughout.

Various example embodiments address technical problems associated with determining the onset of a thermal runaway event. As understood by those of skill in the field to which the present disclosure pertains, there are numerous scenarios in which it may be advantageous to detect thermal runaway in its early stage, providing an opportunity to mitigate the hazardous condition before the thermal runaway becomes irreversible.

In general, batteries (e.g., lithium-ion batteries, lithium-polymer batteries, etc.) may undergo a chemical reaction within a battery cell to supply power to various devices. Devices requiring substantial amounts of power, such as electric vehicles, may contain tens or even hundreds of battery cells in a battery pack.

Battery cells utilizing chemical reactions to generate power may be susceptible to a number of dangerous conditions. One example dangerous battery cell condition that may result from various forms of stress and/or abuse is thermal runaway. In certain circumstances, the movement of electrons and lithium ions in the battery cell may produce heat faster than the battery pack can dissipate the generated heat. Once the internal temperature of the battery cell reaches a certain point, the temperature of the battery cell may rise uncontrollably until the battery cell combusts. Not only can this dangerous condition occur in an individual battery cell but thermal runaway can cause an uncontrollable rise in temperature in the battery cells commonly contained within a battery pack, causing neighboring battery cells to also enter into thermal runaway. Eventually, a battery cell and/or battery pack, may combust causing an extremely hazardous condition. A battery cell may progress through the stages of thermal runaway rapidly, providing little time to detect and mitigate the hazardous condition before the chain reaction is irreversible.

In some instances, the stress and abuse on the battery cells resulting in thermal runaway may be immediate and apparent. For example, a battery cell on an electric vehicle may be punctured or ruptured by flying debris, leading to a thermal runaway event. In other instances, long-term abuse of a battery cell or cells over an extended period of time may lead to thermal runaway. Overcharging, over-discharging, exposure to high and low temperatures, impacts to the battery pack, and/or physical damage to the battery cells, may all affect the internal operation of the battery cells, especially when the abuse occurs over an extended period of time.

One instance in which stress or abuse may lead to thermal runaway is mechanical abuse. In some instances, mechanical abuse, such as a crushing force on a battery cell may lead to an internal short circuit. A short circuit may, in turn, increase the internal heat in the battery cell, triggering a thermal runaway condition. Another example stress or abuse may be electrical abuse, such as chronic overcharging or discharging. In some instances, chronic overcharging and/or discharging may lead to plating and the formation of dendrites, which may subsequently cause short circuits. In addition, many stresses and/or abuses experienced over an extended period of time may cause the chemical properties of the chemicals within the battery cell to slowly change over time. Due to the concealed nature of many of these factors and the sudden onset of thermal runaway, it can be difficult to predict and/or detect a thermal runaway event before it is too late.

A deteriorating battery cell may progress through various stages of battery decay on the way to thermal runaway. For example, the battery cell may experience electrolysis, electrolyte vaporization, and first venting before entering into thermal runaway. Each stage is evidenced by particular characteristics, such as a particular range of temperatures, pressures, and the presence of certain gases. At first venting, for example, gases such as ethylene carbonate (EC), diethyl carbonate (DEC), dimethyl carbonate (DMC) and ethyl methyl carbonate (EMC) may be released from the battery cell.

Current thermal runaway detection systems may utilize various sensors in close proximity to the battery cells to determine the condition of the battery cell based on the physical characteristics around the battery cell. For example, a temperature sensor may be placed on or near the surface of the battery cell. When the temperature measurement exceeds a pre-determined max operating temperature, the thermal runaway detection system may issue a warning or alert. Similarly, pressure sensors may be placed on or near the surface of the battery cell and may be configured to transmit an alert of thermal runaway when the pressure within a battery pack exceeds a pre-determined max operating pressure. Detection systems utilizing temperature sensors and pressure sensors often provide an alert of the onset of thermal runaway once it is too late. For example, temperature sensors are often placed near the battery cells. Temperature sensors near but outside of the battery cells may not detect an increase in temperature outside of the battery cells until after the interior temperature of the battery cell is already rising at an irreversible rate.

Some example thermal runaway detection systems detect smoke as an indicator of the onset of thermal runaway. Smoke detection as an indicator of thermal runaway may be susceptible to false alarms, especially in the context of an electric vehicle. For example, in some examples, smoke from the surrounding environment may be allowed to penetrate the battery pack where the thermal runaway detection system is operating, causing a false alarm to be issued. In addition, smoke may not be emitted from a battery cell until later in the progression of thermal runaway, often after thermal runaway has progressed to a point that mitigating the hazardous condition may be difficult or impossible.

Due to the chain-reaction nature of a thermal runaway event, often, once the thermal runaway event has started, it may not be stopped. As such, in some instances the battery cell will continue to overheat and eventually combust even after the condition is detected and the warning issued. Additionally, the overheating and combustion from a single battery cell may propagate to adjacent battery cells, in some instances leading to a battery pack explosion. Such characteristics of thermal runaway require that thermal runaway be detected at an early stage, when mitigating actions may still be taken.

The various example embodiments described herein utilize various techniques to detect thermal runaway in a battery cell in the early stages, enabling mitigating actions to be taken before the thermal runaway is irreversible. For example, in some embodiments, the thermal runaway detection system may include a light source configured to transmit light across a spectrum of wavelengths. The thermal runaway detection system may further include an emitted light receiver including one or more optical fibers positioned to receive the transmitted light at a first end of the optical fibers. The incident light received at the optical fiber may be directed toward a second end of the optical fiber wherein each optical fibers terminates at a photodiode.

In some example embodiments described herein, the thermal runaway detection system may utilize filtering mechanisms, such as a fiber Bragg grating, to reflect certain wavelengths of light within the optical fiber. The received light reaching the photodiodes may be analyzed by a processor to detect the presence of a particular gas, such as those released by a deteriorating battery cell during first venting. In the presence of certain gases, the transmitted light emitted by the light source may encounter molecules of the gas. Depending on the type of gas, certain wavelengths of light may be reflected or absorbed, thus, never reaching the emitted light receiver. Utilizing the filtering mechanism in-line with the optical fibers and the output readings from the optically connected photodiodes, a controller or other processing device may determine the presence of a specific gas, such as those released during first venting, by comparing the received light spectrum with the spectral signature of a target gas, thus signaling the onset of thermal runaway.

As a result of the herein described example embodiments and in some examples, a thermal runaway detection system may detect thermal runaway at an earlier stage of progression and with greater accuracy. Detecting thermal runaway at an early stage may enable a battery management system to mitigate the hazardous condition before the thermal runaway becomes irreversible.

Referring now to FIG. 1, an example emitted light receiver 100 is provided. As depicted in FIG. 1, the example emitted light receiver comprises a plurality of optical fibers 104a-104d. Each optical fiber includes a first end (e.g., fiber receiving end 102a-102d) positioned at a receiving surface 108 and directed to receive light 112 from a light source 114. In addition, each optical fiber 104a-104d includes a second end terminating at a receiving photodiode 106a-106d.

As depicted in FIG. 1, the example emitted light receiver 100 includes a plurality of optical fibers 104a-104d. An optical fiber 104a-104d may be any cable, cord, wire, line, or other fiber configured to transmit light between the two ends of the optical fiber 104a-104d. An optical fiber 104a-104d may comprise glass, silica, plastic, or other material configured to transmit light between the two ends. In some embodiments, the optical fiber 104a-104d may act as a wave guide facilitating the transmission of light received at the fiber receiving end 102a-102d to the photodiodes 106a-106d placed at the second end of the optical fiber 104a-104d. In some embodiments, the optical fiber 104a-104d may utilize principles of optical physics, such as total internal reflection to transmit light from one end of the optical fiber 104a-104d to the other. Thus, light 112 entering the optical fiber 104a-104d at the fiber receiving end 102a-102d may be transmitted to the photodiodes 106a-106d with minimal loss. Although FIG. 1 depicts an example emitted light receiver 100 comprising four optical fibers 104a-104d, an emitted light receiver 100 may comprise one or more optical fibers (e.g., optical fiber 104a-104d).

As further depicted in FIG. 1, the example emitted light receiver 100 includes a plurality of photodiodes 106a-106d. A photodiode 106a-106d may be any device, sensor, or other structure that produces an electric current in an instance in which the photodiode 106a-106d is exposed to light. In some embodiments, the photodiode 106a-106d may be a light sensitive semiconductor diode that creates an electron-hole pair at the p-n junction when a photon of sufficient energy strikes the diode. In some embodiments, the electric current output by the photodiode 106a-106d may be proportional to the intensity of the light received at the photodiode 106a-106d. For example, the electric current output by the photodiode 106a-106d may increase as the number of photons that strike the photodiode 106a-106d per second increases. In such an embodiment, the electric current output from the one or more photodiodes 106a-106d may be used to determine the intensity of light striking the photodiode 106a-106d. Although FIG. 1 depicts an example emitted light receiver 100 comprising four photodiodes 106a-106d, an emitted light receiver 100 may comprise one or more photodiodes 106a-106d. In addition, although FIG. 1 depicts one photodiode 106a-106d per optical fiber 104a-104d, a photodiode 106a-106d may be associated with one or more optical fibers 104a-104d and/or one or more photodiodes may be associated with an optical fiber 104a-104d.

As further depicted in FIG. 1, the photodiodes 106a-106d of the example emitted light receiver 100 are attached to a photodiode circuit board 110. A photodiode circuit board 110 may be any structure or device configured to electrically connect the one or more photodiodes (e.g., photodiodes 106a-106d) to each other and/or to one or more external devices, such that the electrical output from the photodiodes may be received and further analyzed. In some embodiments, the photodiode circuit board 110 may further include a microcontroller, central processing unit (CPU), and/or other processor (e.g., controller 212 as described in relation to FIG. 2). In some embodiments, the photodiode circuit board 110 may further include ports and/or other connectors utilized to optically couple the one or more optical fibers 104a-104d to the one or more photodiodes 106a-106d such that light received at the fiber receiving end 102a-102d of the optical fiber 104a-104d may be transmitted through the one or more optical fibers 104a-104d and received by the one or more photodiodes 106a-106d.

As further depicted in FIG. 1, a light source 114 may be any single light source or array of light sources configured to produce light 112 directed toward the example emitted light receiver 100. The light source 114 may be any device, bulb, semiconductor, diode, laser, or other photon-emitting structure configured to output light 112. The light source 114 may be configured to output light 112 at a specific wavelength or spectrum of wavelengths. For example, the light source 114 may be configured to output light 112 having a wavelength between 0.75 micrometers and 15 micrometers. In some embodiments, the light source 114 may be configured to output the spectrum of wavelengths simultaneously. In some embodiments, the light source may be configured to output the spectrum of wavelengths sequentially, altering the wavelength of the output light 112 over time. In some embodiments, the light source 114 may comprise an array of light emitting diodes (e.g., light source 202 as further described in relation to FIG. 2). The light source 114 may be configured to output light 112 in any spectrum or range of spectrums, such as in the visible spectrum (400 nanometers-750 nanometers), ultraviolet light (100-400 nanometers), and/or infrared light (750 nanometers-1,000,000 nanometers). The light source 114 may be configured to direct the light 112 toward the emitted light receiver 100.

As described above, the light 112 produced by the light source 114 may be directed toward the receiving surface 108 of the one or more fiber receiving ends 102a-102d. The receiving surface may be any plane or surface to which the fiber receiving ends 102a-102d may terminate. In some embodiments, the receiving surface 108 may include ports and/or connectors, attaching the optical fibers 104a-104d to the receiving surface 108 and exposing the one or more fiber receiving ends 102a-102d. In some embodiments, the receiving surface 108 may further include lenses, filters, or other optical devices configured to facilitate the transmission of light 112 into the optical fibers the one or more fiber receiving ends 102a-102d. Although pictured as a structure in FIG. 1, in some embodiments, the receiving surface 108 may simply comprise the fiber receiving ends 102a-102d of the optical fibers 104a-104d.

Figure 2:
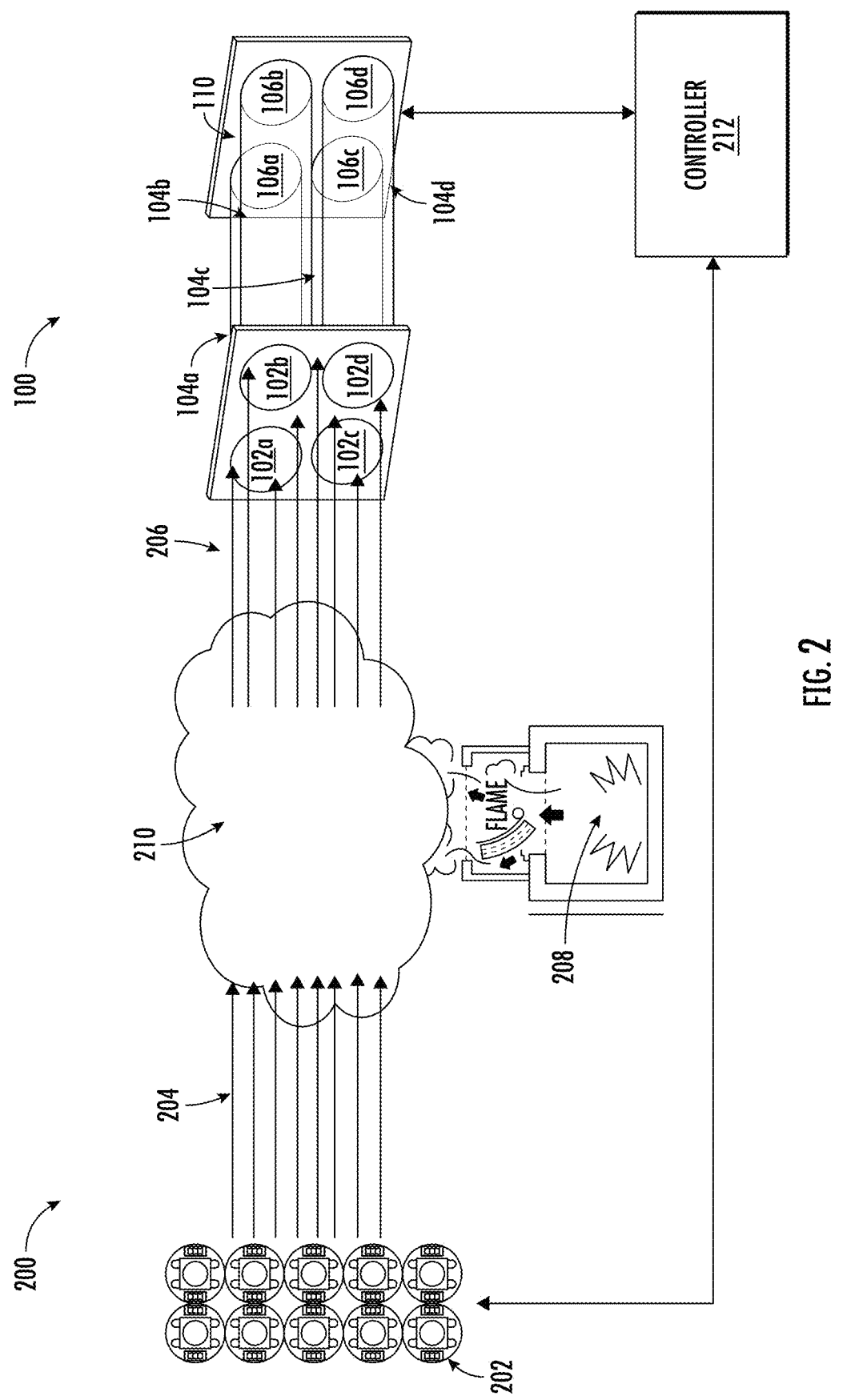
FIG. 2 illustrates a system-level diagram of an example thermal runaway detection system in accordance with an example embodiment of the present disclosure.

Referring now to FIG. 2, an example thermal runaway detection system 200 is provided. As depicted in FIG. 2, the example thermal runaway detection system 200 comprises an emitted light receiver 100 positioned to receive light (e.g., received light 206) from a light source 202 producing transmitted light 204. In addition, the example thermal runaway detection system 200 includes a controller 212 communicatively connected to a photodiode circuit board 110 and the light source 202. As further depicted in FIG. 2, the example thermal runaway detection system 200 may be positioned proximate a battery cell 208, such that in an instance in which the battery cell 208 emits one or more gases, the transmitted light 204 interacts with the gas cloud 210 emitted from the battery cell 208 before it is received by the emitted light receiver 100 as received light 206.

As depicted in FIG. 2, the example thermal runaway detection system 200 comprises a light source 202 comprising an array of light emitting diodes (LEDs). As described in relation to FIG. 1, the light source 202 may be configured to emit transmitted light 204 across a spectrum of wavelengths. In some embodiments, a light source 202 may utilize an array of LEDs to simultaneously transmit light of varying wavelengths. As such, a spectrum of transmitted light 204 comprising light of varying wavelengths may be transmitted. For example, in some embodiments, the transmitted light may consist of light with wavelengths ranging from 0.75 micrometers (750 nanometers) to 15 micrometers (15,000 nanometers).

As further depicted in FIG. 2, the light source 202 is directed toward the emitted light receiver 100. In some embodiments, the light source 202 may be directional, meaning the projection of the transmitted light 204 is in a direction, such as a light beam. In such an instance, the direction of the transmitted light 204 is aimed at the emitted light receiver 100. In some embodiments, the light source 202 may be omni-directional, meaning the projection of the transmitted light 204 is in all directions and is not aimed at a single object such as the emitted light receiver 100.

As further depicted in FIG. 2, the transmitted light 204 from the light source 202 may be transmitted near a battery cell 208. A battery cell 208 may be any electrochemical device utilizing chemical reactions to generate electrical energy. Chemical reactions within a battery cell 208 may involve transmitting ions between a positively charged electrode (cathode) and a negatively charged electrode (anode). When a battery cell 208 provides power to a load, the flow of the electrons from the anode to the cathode generates electric current flowing from the cathode to the anode. A battery cell may contain any of a large variety of chemical compositions (e.g., lithium-nickel-manganese-cobalt oxides, lithium-iron phosphates, etc.). A battery cell 208 facilitating such chemical reactions may be susceptible to a decay process resulting in thermal runaway as further

Figure 6:
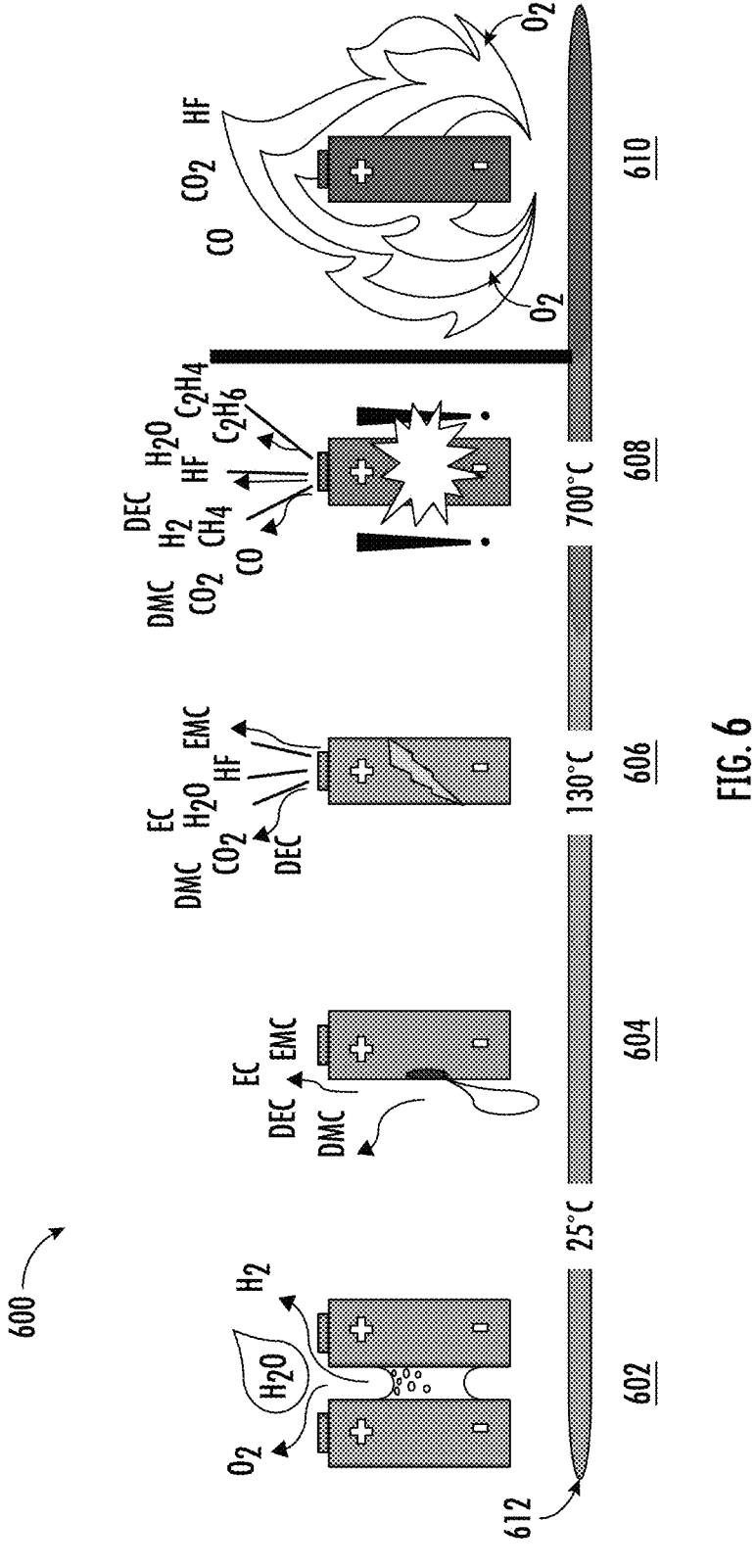
FIG. 6 illustrates an example thermal runaway progression in accordance with an example embodiment of the present disclosure.

9 described in relation to FIG. 6. Also described in relation to FIG. 6, leading up to and during thermal runaway, gases (e.g., gas cloud 210) may be released from a battery cell 208, releasing the gas into the environment immediately surrounding the battery cell 208.

A battery cell 208 may take any form, including but not limited to cylindrical cells, prismatic cells, pouch cells, etc. Some devices requiring large amounts of power, such as an electric vehicle may contain tens or hundreds of battery cells 208 in a battery pack. The battery cells 208 within a battery pack may be electrically connected in parallel and/or series to provide an accumulated power output to the operating device (e.g., an electric vehicle). In some embodiments, the thermal runaway detection system 200 may be placed within the battery pack near the plurality of battery cells 208.

As further depicted in FIG. 2, the placement of the thermal runaway detection system 200 on or near a battery cell 208 and/or a battery pack enables the transmitted light 204 generated by the light source 202 to interact with any gases (e.g., gas cloud 210) emitted by the battery cell 208. In an instance in which a gas cloud 210 is present, the transmitted light 204 may be reflected, absorbed, scattered, refracted, diffracted, or otherwise altered. The interaction with the gas cloud 210 may change one or more properties of the transmitted light 204, resulting in a received light 206 having different physical properties than the transmitted light 204 when reaching the emitted light receiver 100. For example, in some embodiments, certain wavelengths of light within the transmitted light 204 spectrum may be absorbed, scattered, reflected, etc. such that the received light 206 arriving at the emitted light receiver 100 may be devoid of the absorbed, scattered, reflected, etc. wavelengths of light. As further described in relation to FIG. 8A-FIG. 8D, in some embodiments, a specific gas may be identified based on the absorbed, scattered, reflected, etc. wavelengths of light.

As further depicted in FIG. 2, the example thermal runaway detection system 200 includes a controller 212. A controller 212 (e.g., processor) may be any means such as a processor, device, or circuitry embodied in either hardware or a combination of hardware and software that is configured to issue commands and receive status and measurement data from the emitted light receiver 100 and the light source 202. The controller 212 may comprise a configuration as shown and described in relation to FIG. 3. While FIG. 3 provides an example controller 212, it is noted that the scope of the present disclosure is not limited to the example shown in FIG. 3.

Figure 3:
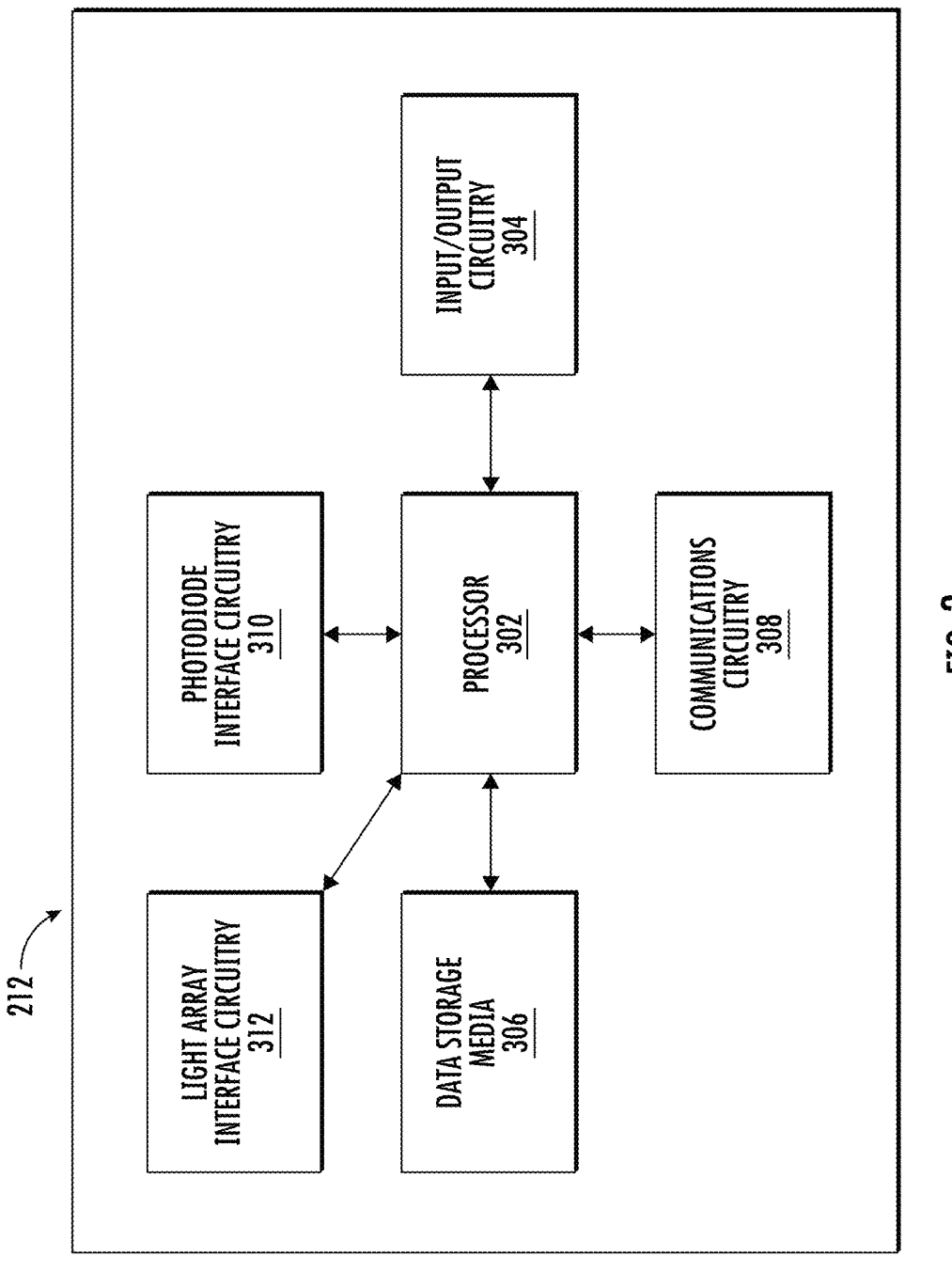
FIG. 3 illustrates an example block diagram showing example components of an example controller in accordance with an example embodiment of the present disclosure.

Referring now to FIG. 3, FIG. 3 illustrates an example controller 212 in accordance with at least some example embodiments of the present disclosure. The controller 212 includes processor 302, input/output circuitry 304, data storage media 306, communications circuitry 308, photodiode interface circuitry 310, and light array interface circuitry 312. In some embodiments, the controller 212 is configured, using one or more of the sets of circuitry 302, 304, 306, 308, 310, and/or 312, to execute and perform the operations described herein.

Although components are described with respect to functional limitations, it should be understood that the particular implementations necessarily include the use of particular computing hardware. It should also be understood that in some embodiments certain of the components described herein include similar or common hardware. For example, two sets of circuitry may both leverage use of the same processor(s), network interface(s), storage medium(s), and/ or the like, to perform their associated functions, such that duplicate hardware is not required for each set of circuitry. The user of the term "circuitry" as used herein with respect to components of the apparatuses described herein should therefore be understood to include particular hardware configured to perform the functions associated with the particular circuitry as described herein.

Particularly, the term "circuitry" should be understood broadly to include hardware and, in some embodiments, software for configuring the hardware. For example, in some embodiments, "circuitry" includes processing circuitry, storage media, network interfaces, input/output devices, and/or the like. Alternatively or additionally, in some embodiments, other elements of the controller 212 provide or supplement the functionality of other particular sets of circuitry. For example, the processor 302 in some embodiments provides processing functionality to any of the sets of circuitry, the data storage media 306 provides storage functionality to any of the sets of circuitry, the communications circuitry 308 provides network interface functionality to any of the sets of circuitry, and/or the like.

In some embodiments, the processor 302 (and/or co-processor or any other processing circuitry assisting or otherwise associated with the processor) is/are in communication with the data storage media 306 via a bus for passing information among components of the controller 212. In some embodiments, for example, the data storage media 306 is non-transitory and may include, for example, one or more volatile and/or non-volatile memories. In other words, for example, the data storage media 306 in some embodiments includes or embodies an electronic storage device (e.g., a computer readable storage medium). In some embodiments, the data storage media 306 is configured to store information, data, content, applications, instructions, or the like, for enabling the controller 212 to carry out various functions in accordance with example embodiments of the present disclosure.

The processor 302 may be embodied in a number of different ways. For example, in some example embodiments, the processor 302 includes one or more processing devices configured to perform independently. Additionally or alternatively, in some embodiments, the processor 302 includes one or more processor(s) configured in tandem via a bus to enable independent execution of instructions, pipelining, and/or multithreading. The use of the terms "processor" and "processing circuitry" should be understood to include a single core processor, a multi-core processor, multiple processors internal to the controller 212, and/or one or more remote or "cloud" processor(s) external to the controller 212.

In an example embodiment, the processor 302 is configured to execute instructions stored in the data storage media 306 or otherwise accessible to the processor. Alternatively or additionally, the processor 302 in some embodiments is configured to execute hard-coded functionality. As such, whether configured by hardware or software methods, or by a combination thereof, the processor 302 represents an entity (e.g., physically embodied in circuitry) capable of performing operations according to an embodiment of the present disclosure while configured accordingly. Alternatively or additionally, as another example in some example embodiments, when the processor 302 is embodied as an executor of software instructions, the instructions specifically configure the processor 302 to perform the algorithms embodied in the specific operations described herein when such instructions are executed.

As one particular example embodiment, the processor 302 is configured to perform various operations associated with detecting thermal runaway in a battery cell (e.g., battery cell 208). In some embodiments, the processor 302 includes hardware, software, firmware, and/or a combination thereof that causes a light source (e.g., light source 202) to emit light (e.g., transmitted light 204) comprising a transmitted spectrum of wavelengths. Additionally or alternatively, in some embodiments, the processor 302 includes hardware, software, firmware, and/or a combination thereof, that receives, from a photodiode (e.g., receiving photodiode 106a-106d) optically coupled to a sensing fiber (e.g., optical fiber 104a-104d), an electrical output corresponding to an intensity of light received at the photodiode, wherein the sensing fiber comprises a first end (e.g., fiber receiving end 102a-102d) and a second end, wherein the sensing fiber is positioned to receive the light emitted by the light source at the first end, wherein the sensing fiber is optically coupled to the photodiode at the second end, and wherein the sensing fiber comprises a filtering mechanism (e.g., fiber Bragg grating 406 as described in relation to FIG. 4 and fiber Bragg grating 506 as described in relation to FIG. 5A-FIG. 5B) configured to reflect a portion of the transmitted spectrum of wavelengths of the light. Additionally or alternatively, in some embodiments, the processor 302 includes hardware, software, firmware, and/or a combination thereof, that identifies a gas (e.g., gas cloud 210) based on the electrical output of the photodiode. Additionally or alternatively, in some embodiments, the processor 302 includes hardware, software, firmware, and/or a combination thereof, that detects thermal runaway in the battery cell based at least in part on identifying the gas.

In some embodiments, the controller 212 includes input/output circuitry 304 that provides output to the user and, in some embodiments, to receive an indication of a user input. In some embodiments, the input/output circuitry 304 is in communication with the processor 302 to provide such functionality. The input/output circuitry 304 may comprise one or more user interface(s) (e.g., user interface) and in some embodiments includes a display that comprises the interface(s) rendered as a web user interface, an application user interface, a user device, a backend system, or the like. The processor 302 and/or input/output circuitry 304 comprising the processor may be configured to control one or more functions of one or more user interface elements through computer program instructions (e.g., software and/or firmware) stored on a memory accessible to the processor (e.g., data storage media 306, and/or the like). In some embodiments, the input/output circuitry 304 includes or utilizes a user-facing application to provide input/output functionality to a client device and/or other display associated with a user.

In some embodiments, the controller 212 includes communications circuitry 308. The communications circuitry 308 includes any means such as a device or circuitry embodied in either hardware or a combination of hardware and software that is configured to receive and/or transmit data from/to a network and/or any other device, circuitry, or module in communication with the controller 212. In this regard, the communications circuitry 308 includes, for example in some embodiments, a network interface for enabling communications with a wired or wireless communications network. Additionally or alternatively in some embodiments, the communications circuitry 308 includes one or more network interface card(s), antenna(s), bus(es), switch(es), router(s), modem(s), and supporting hardware, firmware, and/or software, or any other device suitable for enabling communications via one or more communications network(s). Additionally or alternatively, the communications circuitry 308 includes circuitry for interacting with the antenna(s) and/or other hardware or software to cause transmission of signals via the antenna(s) or to handle receipt of signals received via the antenna(s). In some embodiments, the communications circuitry 308 enables transmission to and/or receipt of data from a client device in communication with the controller 212.

The photodiode interface circuitry 310 includes hardware, software, firmware, and/or a combination thereof, that supports various functionality associated with command and control of a photodiode and or array of photodiodes, for example attached to a printed circuit board (e.g., photodiode circuit board 110). For example, in some embodiments, the photodiode interface circuitry 310 includes hardware, software, firmware, and/or a combination thereof to issue commands directly to the one or more photodiodes, and/or issue commands to the printed circuit board comprising the one or more photodiodes. Commands issued by the photodiode interface circuitry 310 may include configuring parameters of the photodiodes, configuring feedback parameters of the photodiodes, or other similar commands. Additionally or alternatively, in some embodiments, the photodiode interface circuitry 310 includes hardware, software, firmware, and/or a combination thereof, to receive electrical output of the one or more photodiodes and/or the printed circuit board comprising the one or more photodiodes. In some embodiments, the electrical output received by the photodiode interface circuitry 310 may correspond with the intensity of light received by the photodiode. In some embodiments, the electrical output may be received as an analog signal by the photodiode interface circuitry 310 while in other embodiments, the electrical output may be received as a digital signal at the photodiode interface circuitry 310.

The light array interface circuitry 312 includes hardware, software, firmware, and/or a combination thereof, that supports various functionality associated with command and control of a light source (e.g., light source 202), for example an LED and/or an array of LEDs. In some embodiments, the light array interface circuitry 312 includes hardware, software, firmware, and/or a combination thereof to issue commands directly to the light source, and/or issue commands to circuitry providing an interface with the light source. Commands issued by the light array interface circuitry 312 may include configuration of parameters associated with the light source, such as intensity of the light source, periodic durations at which the light is illuminated, parameters related to the wavelength of the emitted light, or other similar commands. For example, in some embodiments, the light array interface circuitry 312 may enable and disable LEDs in an array of LEDs to control the spectrum of wavelengths emitted by the light source.

Additionally or alternatively, in some embodiments, one or more of the sets of circuitry 302-312 are combinable. Additionally or alternatively, in some embodiments, one or more of the sets of circuitry perform some or all of the functionality described associated with another component. For example, in some embodiments, one or more sets of circuitry 302-312 are combined into a single module embodied in hardware, software, firmware, and/or a combination thereof. Similarly, in some embodiments, one or more of the sets of circuitry, for example photodiode interface circuitry 310, and/or light array interface circuitry 312, is/are combined such that the processor 302 performs one or more of the operations described above with respect to each of these circuitry individually.

Figure 4:
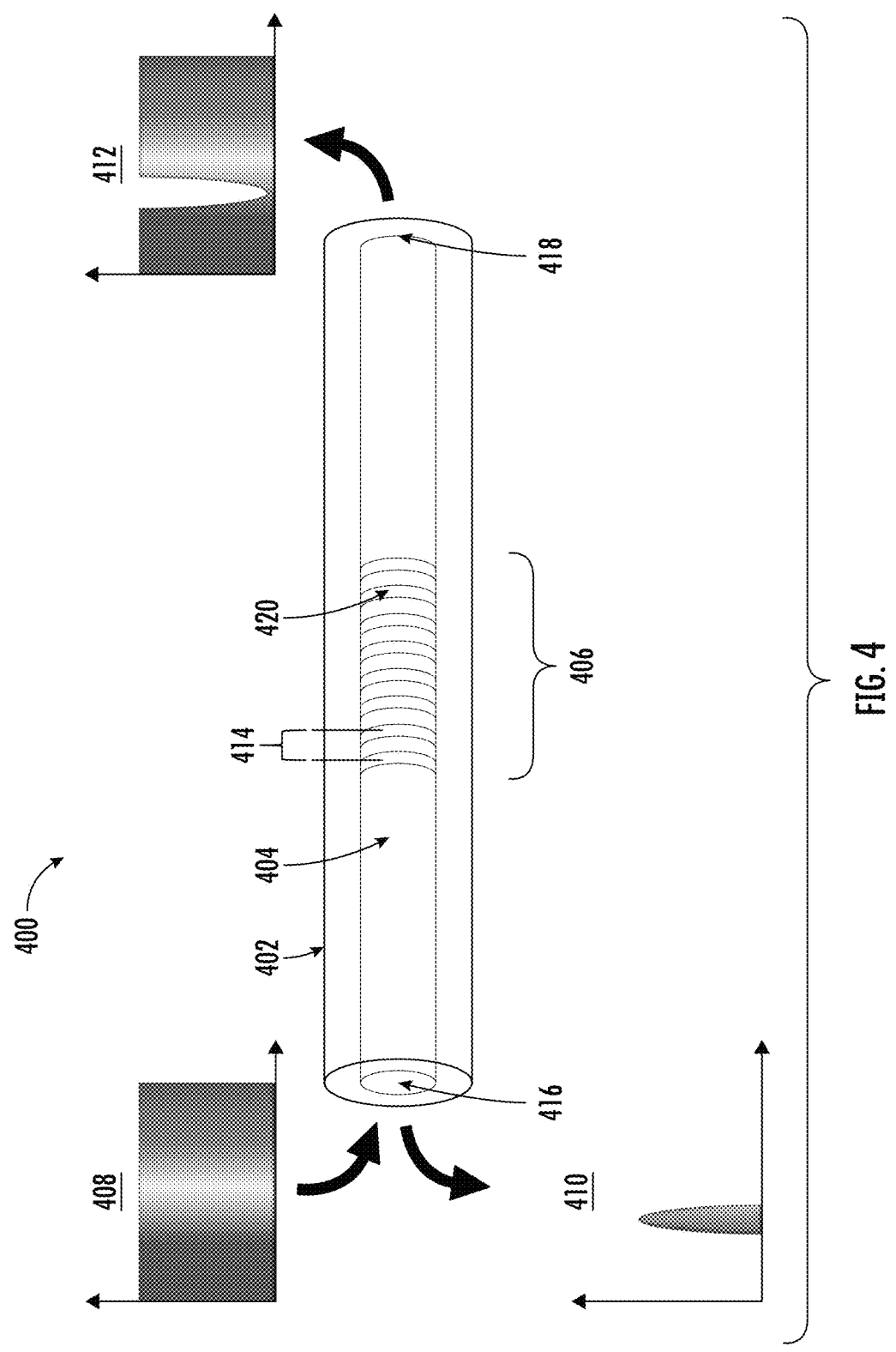
FIG. 4 illustrates an example optical fiber including an example fiber Bragg grating in accordance with an example embodiment of the present disclosure.

Referring now to FIG. 4, an example optical fiber 400 (e.g., optical fiber 104a-104d) is provided. As depicted in FIG. 4, the example optical fiber 400 includes a cylindrical fiber core 404 enclosed in a cylindrical cladding 402. The fiber core 404 of the example optical fiber 400 further includes a fiber Bragg grating 406 having a grating period 414. As shown in FIG. 4, an incident light spectrum 408 enters the optical fiber 400 through the fiber core 404 at a receiving end 416. A portion of the incident light spectrum 408 is reflected by the fiber Bragg grating 406 and an example spectrum is depicted in FIG. 4 as the reflected light spectrum 410. The portion of the incident light spectrum 408 transmitted through the optical fiber 400 is shown as the received light spectrum 412 emerging from the terminal end 418 of the optical fiber 400.

As depicted in FIG. 4, the example optical fiber 400 includes a fiber core 404 and cladding 402. An optical fiber 400 may be any cord, wire, fiber, waveguide, or other structure configured to transmit light from a receiving end 416 at which the light enters the optical fiber 400 to a terminal end 418 at which the transmitted light reaches a destination, for example a photodiode. The example optical fiber 400 depicted in FIG. 4 includes a cylindrical fiber core 404 enclosed in a cladding 402. The fiber core 404 and cladding 402 may be selected such that light entering the fiber core 404 experiences total internal reflection due to the difference in the refractive index between the fiber core 404 and the cladding 402. In some embodiments, the fiber core 404 may comprise glass or plastic. In some embodiments, the cladding 402 may comprise a silica material, such as a doped silica.

As further depicted in FIG. 4, the example optical fiber 400 includes a fiber Bragg grating 406. A fiber Bragg grating 406 may be any structure, material, anomaly, or other feature within the fiber core 404 of the optical fiber 400 causing the fiber core to reflect certain wavelengths of light transmitted through the fiber core 404. In general, a fiber Bragg grating 406 comprises a series of changes to the refractive index (e.g., refractive index change 420) of the fiber core 404. Normally, the fiber core 404 exhibits a uniform or near uniform refractive index across the length of the fiber core 404. By introducing a change in the refractive index (e.g., refractive index change 420) into the fiber core 404, light propagating through the fiber core 404 may experience reflection and/or refraction when encountering the change in refractive index. As depicted in FIG. 4, the refractive index changes 420 may be placed in the fiber core 404 at a grating period 414. A fiber Bragg grating 406 will reflect wavelengths of light that match the grating period 414. Other wavelengths of light will continue to propagate through the fiber core 404.

The fiber Bragg grating 406 may be created by inscribing periodic variations of refractive index (e.g., refractive index change 420) in the fiber core 404 of the optical fiber 400. In one example embodiment, variations of refractive index are inscribed in the fiber core by masking or interference. In an instance in which the material of the fiber core is photosensitive, such as germanium doped fiber, the refractive index of the fiber core 404 may be changed by exposing the fiber core 404 to ultraviolet (UV) light. Masking may involve placing a photomask between the fiber core 404 and the UV light source. The photomask may include slots or holes, exposing the refractive index change 420 portions of the fiber core 404 to the UV light while leaving the other portions of the fiber core 404 unchanged. Photomasks may be necessary in creating a chirped fiber Bragg grating, such as the fiber Bragg grating 506 of FIG. 5A-FIG. 5B, where the refractive changes are not periodic. Interference may be used to inscribed refractive changes in the fiber core 404 at a uniform interval or period. Interference may involve splitting a UV laser into two beams that interfere with each other at uniform period across the fiber core 404. The areas of interference are exposed to a greater intensity of UV light at the interference point causing a change to the refractive index of the fiber core 404 over a uniform period.

FIG. 4 further depicts an incident light spectrum 408 entering the fiber core 404 at the receiving end 416. The incident light spectrum 408 depicts a range of lights having different wavelengths entering the fiber core 404. In some embodiments, the incident light spectrum 408 may include the range of visible light, for example, light with wavelengths between 400 and 750 nanometers. In some embodiments, the incident light spectrum 408 received at the receiving end 416 of the fiber core 404 may include infrared light, for example, light having wavelengths between 750 nanometers and 15,000 nanometers.

An example reflected light spectrum 410 is further depicted in FIG. 4. As shown in FIG. 4, the reflected portion of the incident light spectrum 408 shown in the reflected light spectrum 410 corresponds with the wavelength of light reflected by the fiber Bragg grating 406. The wavelength of light reflected varies based on the grating period 414 of the fiber Bragg grating 406. As further depicted in FIG. 4, the received light spectrum 412 received at the terminal end 418 of the optical fiber 400 corresponds with all other wavelengths of light of the incident light spectrum 408 not reflected by the fiber Bragg grating 406.

In some embodiments, multiple fiber Bragg gratings 406 comprising various grating periods 414 may be inscribed on a single line of optical fiber 400. Each fiber Bragg grating 406 may reflect a different portion of the incident light spectrum 408. Multiple fiber Bragg gratings 406 may result in a significant portion of the incident light spectrum being reflected resulting in a narrow width of wavelengths transmitted through the optical fiber 400.

Figure 5A:
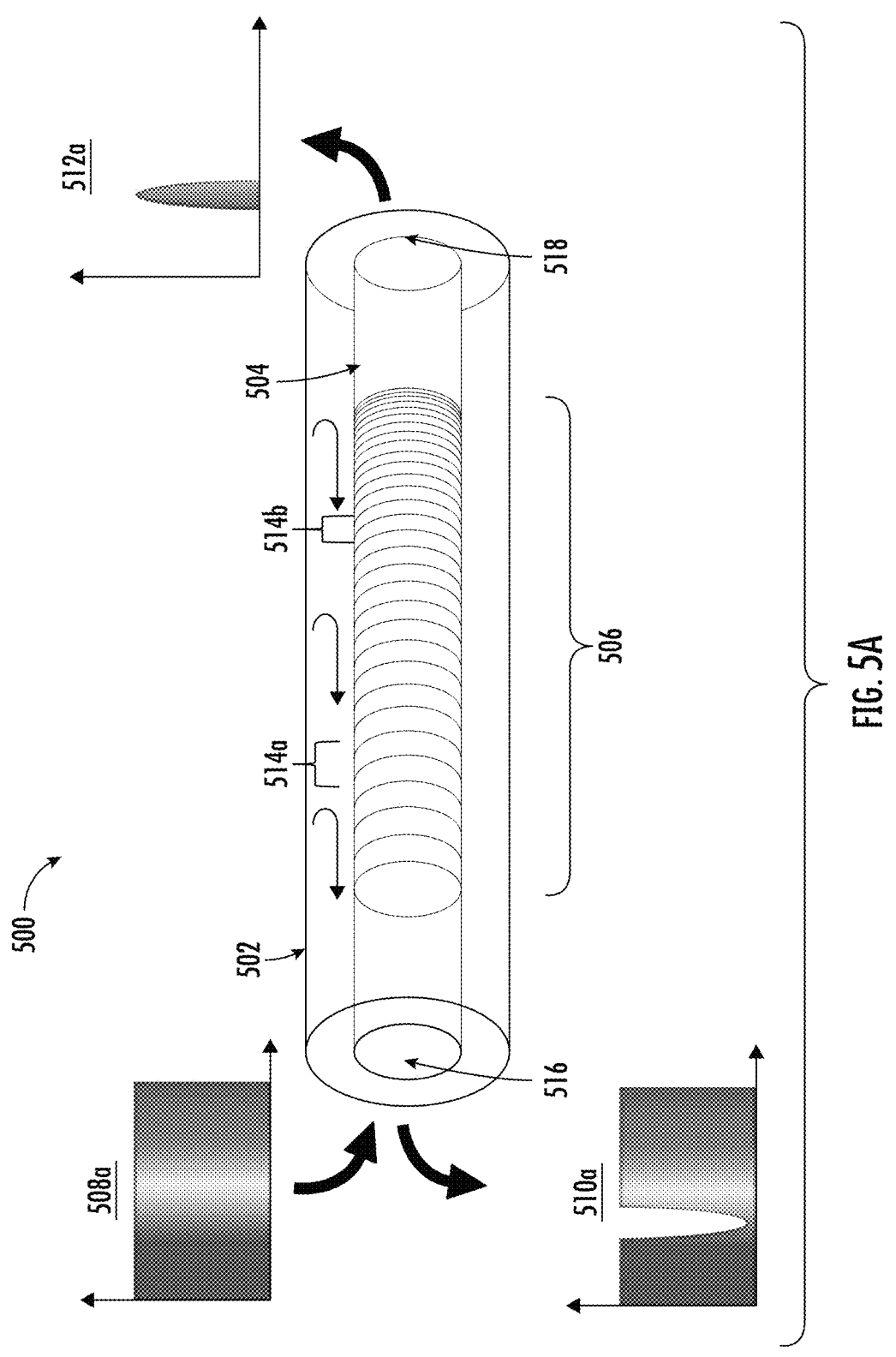
FIG. 5A illustrates another example optical fiber including another example fiber Bragg grating in accordance with an example embodiment of the present disclosure.

Referring now to FIG. 5A, another example optical fiber 500 is provided. The optical fiber 500 as depicted in FIG. 5A consists of a fiber core 504 enclosed in a cladding 502. The fiber core of the example optical fiber further includes a fiber Bragg grating 406 having a non-uniform or chirped grating period 514a, 514b. As shown in FIG. 5A, an incident light spectrum 508a enters the optical fiber 500 through the fiber core 504 at a receiving end 516. A portion of the incident light spectrum 508a is reflected (e.g., reflected light spectrum 510a) by the fiber Bragg grating 506. The portion of the incident light spectrum 508a transmitted through the optical fiber 500 is shown as the received light spectrum 512a emerging from the terminal end 518 of the optical fiber 500.

As depicted in FIG. 5A, the fiber core 504 of the example optical fiber 500 comprises a fiber Bragg grating 506 having a chirped grating period 514a, 514b. A chirped grating period 514a, 514b comprises a linear variation in the grating period of the fiber Bragg grating. For example, as shown in FIG. 5A, the grating period of the fiber Bragg grating 506 becomes smaller (e.g., grating period 514b) as the fiber Bragg grating moves closer to the terminal end 518 when compared with the grating period 514a near the receiving end 516 of the optical fiber 500. The reflected wavelength changes as the grating period of the fiber Bragg grating 506 changes. Thus, in some embodiments, a fiber Bragg grating 506 comprising a chirped grating period 514a, 514b may reflected a broader range of wavelengths of light when compared to a fiber Bragg grating comprising a uniform grating period.

As depicted in FIG. 5A, the fiber Bragg grating 506 comprising a chirped grating period 514a, 514b may reflect a reflected light spectrum 510a of the incident light spectrum 508a comprising a wider range of wavelengths compared to a fiber Bragg grating comprising a uniform grating period. As further depicted in FIG. 5A, the received light spectrum 512a received at the terminal end 518 of the optical fiber 500 may comprise a narrow spectrum of wavelengths of light.

In some embodiments, the same effect may be realized by inscribing multiple fiber Bragg gratings in series, as described in relation to FIG. 5A.

Figure 5B:
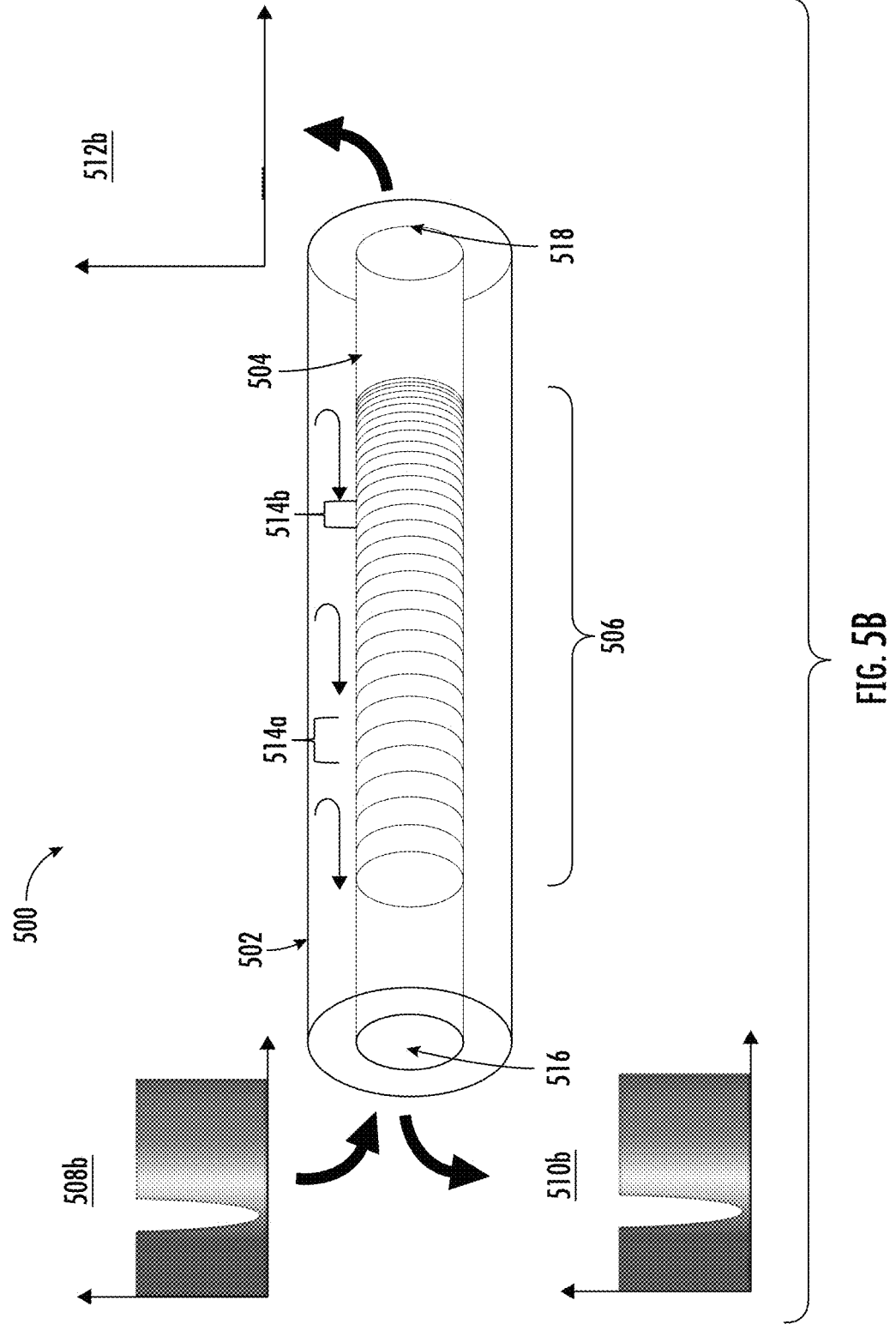
FIG. 5B illustrates an example received light spectrum given an incident light spectrum at the example fiber Bragg grating in accordance with an example embodiment of the present disclosure.

Referring now to FIG. 5B, the fiber Bragg grating 506 comprising a chirped grating period 514a, 514b may be utilized to identify an incident light spectrum 508b having a particular spectrum signature. In some embodiments, the incident light spectrum 508b entering the fiber core 504 of the optical fiber 500 may have a particular spectrum signature. For example, the incident light spectrum may be devoid of light of certain wavelengths. An incident light spectrum 508b may be missing certain wavelengths of light for a variety of reasons. For example, light may be transmitted comprising only certain wavelengths and devoid of log of other wavelengths. As another example, transmitted light may encounter molecules, structures, or other obstructions that reflect, refract, scatter, absorb, diffract, or otherwise alter certain wavelengths of light. As described in relation to FIG. 8A-FIG. 8D, light passing through certain gases may be altered such that certain wavelengths of light fail to transmit through the gas, resulting in a light spectrum signature unique to the gas.

The incident light spectrum 508b of FIG. 5B depicts a light spectrum missing a narrow band of wavelengths. In such an instance in which the fiber Bragg grating 506 is configured to reflect all the wavelengths besides the narrow band missing from the incident light spectrum 508b (as depicted by the reflected light spectrum 510b), all of the incident light spectrum 508b is reflected such that no light transmits through the optical fiber 500 to the terminal end 518 (as depicted by the received light spectrum 512b). In some embodiments, the reception of no light at the terminal end 518 may be an indicator of an incident light spectrum 508b matching the reflected light spectrum 510b.

Utilizing a plurality of optical fibers (e.g., optical fiber 104a-104d) each comprising a fiber Bragg grating (e.g., fiber Bragg grating 406, fiber Bragg grating 506) with a different reflected light spectrum, specific unique identifying points of an incident light spectrum may be identified.

Referring now to FIG. 6, a chart illustrating an example thermal runaway progression 600 in a battery cell is provided. As depicted in FIG. 6, the example thermal runaway progression 600 comprises five stages, for example, electrolysis 602, electrolyte vaporization 604, first venting 606, thermal runaway 608, and catastrophic explosion 610. Each stage of the thermal runaway progression 600 is associated with a certain temperature or range of temperatures within the battery cell, as shown by the temperature scale 612, and other characteristics such as an internal pressure and the presence of certain gases.

As depicted in FIG. 6, the first stage of the example thermal runaway progression 600 is electrolysis 602. During electrolysis 602, the electrolyte begins to break down between the anode and cathode within the battery cells. Electrolysis 602 is characterized by elevated gas levels, specifically elevated gas levels of oxygen and hydrogen. The operating temperature and the pressure readings remain constant, in a normal operating range for the battery cell and the environment during electrolysis. For example, the operating temperature may be between 20° C. and 80° C., while the pressure remains below about 14.5 pounds per square inch.

As further depicted in FIG. 6, the second stage of the example thermal runaway progression is electrolyte vaporization 604. During the electrolyte vaporization 604, the electrolyte between the anode and cathode within the battery cells fully breaks down. Electrolyte vaporization 604 is characterized by elevated levels of ethylene carbonate (EC), dimethyl carbonate (DMC), diethyl carbonate (DEC), and/or ethyl methyl carbonate (EMC). The vaporization stage may also be characterized by an elevated temperature, for example, between 80° C. and 100° C.

As further depicted in FIG. 6, the third stage of the example thermal runaway progression is first venting 606. During the first venting 606, the buildup of gas due to the decomposition of the electrolyte inside the battery cell may cause deformations in the casing of the battery cell and eventual openings in or rupture of the battery cell. First venting 606 is characterized by an initial increase in temperature and elevated gas levels of EC, DMC, DEC, EMC, and carbon dioxide. In addition, first venting may be characterized by an increase in the internal pressure of the interior battery compartment, for example a pressure above 14.5 pounds per square inch. In some embodiments, a temperature between 120° C. and 300° C. within the interior battery compartment may be an indicator that the battery has entered into first venting 606.

As further depicted in FIG. 6, the fourth stage of the example thermal runaway progression is thermal runaway 608. During thermal runaway 608, chemical reactions within the battery cells continue due to an increase in temperature causing a severe and sudden increase of temperature. Once thermal runaway 608, the chain reaction leading to catastrophic explosion 610 is often irreversible. In an instance in which a plurality of battery cells are in close proximity, thermal runaway 608 may spread to neighboring battery cells. Thermal runaway 608 may be characterized by elevated gas levels of EC, DMC, DEC, EMC, methane, carbon monoxide, ethanol, and carbon dioxide. In some embodiments, thermal runaway 608 is characterized by a temperature at or exceeding 300° C. and less than 800° C.

As further depicted in FIG. 6, the final stage of the example thermal runaway progression is catastrophic explosion 610. During catastrophic explosion 610 a battery may catch fire and/or explode creating an extremely dangerous situation. During catastrophic explosion 610 the temperature of the battery cell may exceed 800° C. The uncontrolled combustion during catastrophic explosion 610 is extremely hazardous to the operating device and any people and objects in close proximity.

Figure 7:
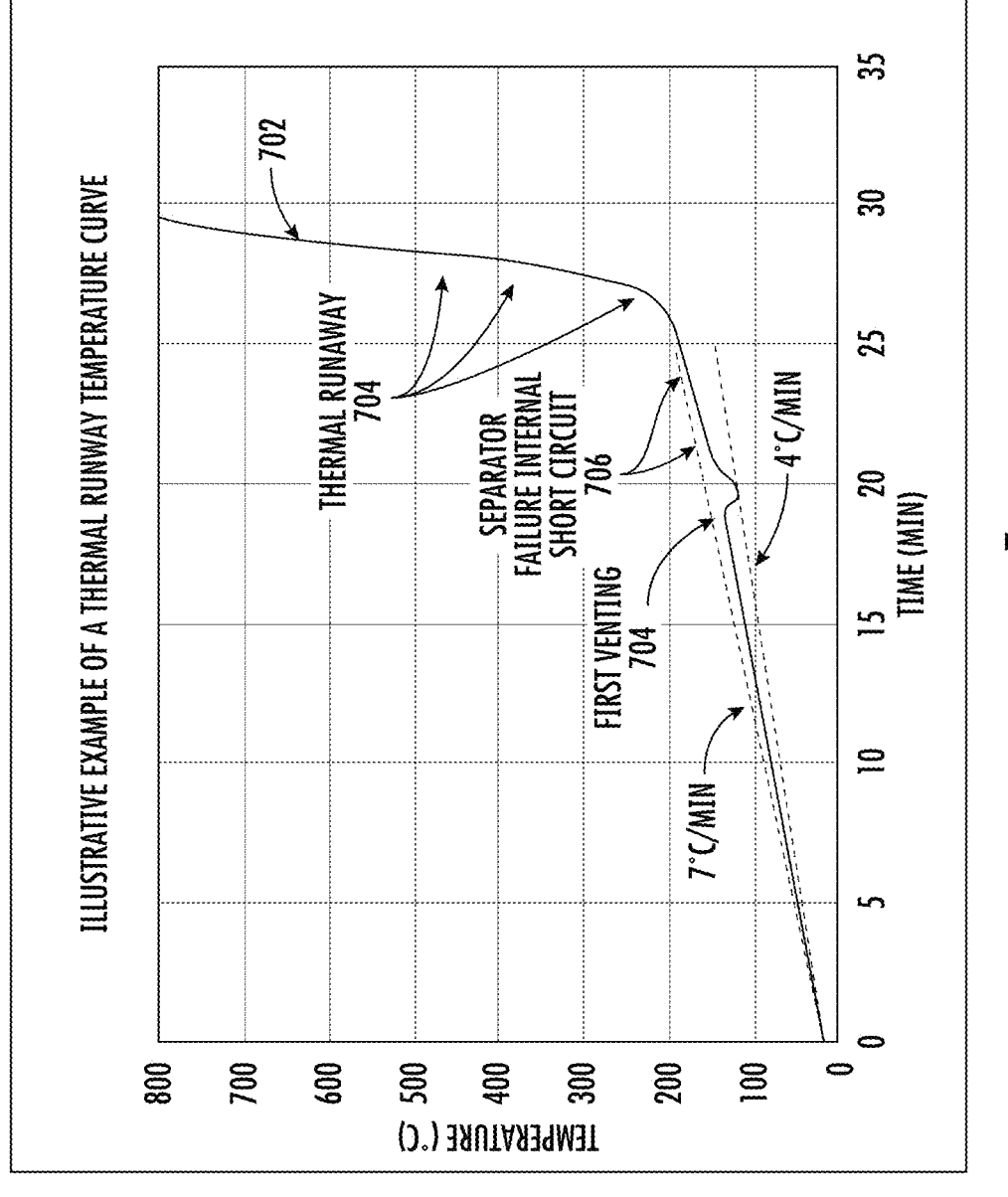
FIG. 7 illustrates an example thermal runaway temperature curve in accordance with an example embodiment of the present disclosure.

Referring now to FIG. 7, an example thermal runaway temperature chart 700 including a thermal runaway temperature curve 702 is provided. The example thermal runaway temperature chart 700 graphs the temperature of a battery cell as it progresses through the stages prior to and eventually entering thermal runaway. The x-axis displays the time in minutes and the y-axis represents the temperature of the battery cell.

As depicted in FIG. 7, the temperature of a battery cell progressing towards thermal runaway 708 increases steadily through the early stages of battery decay (e.g., first venting 704, separator failure/internal short circuit 706). For example, the temperature may increase between about 4° C. and 5° C. every minute during the first 25 minutes of decay. If the hazardous condition is detected during this period, mitigating actions may be taken that may prevent the battery from entering into thermal runaway. However, once the battery enters into thermal runaway 708, the internal temperature of the battery increases rapidly and uncontrollably, for example, at a rate of almost 200° C. per minute. As depicted in FIG. 7, first venting 704 occurs before the drastic increase in temperature and may be accompanied by a slight dip in the internal temperature of the battery cell due to the release of gases. Thus, utilizing the release of gases at first venting 704 may enable the battery decay to be detected before the battery cell enters into thermal runaway.

Referring now to FIG. 8A-FIG. 8D, example spectral signatures 802a-802d for various gases that may be present during the first venting of a battery are provided. Each spectral signature 802a-802d depicts the transmittance (y-axis) with respect to a given wavelength of light in micrometers (x-axis).

As depicted in FIG. 8A-FIG. 8D, the transmittance (y-axis) may refer to the ratio of the intensity of the incident light to the intensity of the received light. In an example embodiments, a light source may produce a transmitted light having an intensity of 100 millicandela at a particular wavelength. In some examples, the transmitted light may travel through a gas and some of the light may be reflected and/or absorbed. If the received light, received at a receiving device, such as a photodiode for the same wavelength has an intensity of only 75 millicandela, then the calculated transmittance is 0.75. Each gas may exhibit a different transmittance for each wavelength of light across a light spectrum. Utilizing a thermal runaway detection system with a light source (e.g., light source 202) transmitting light across a spectrum of wavelengths and an emitted light receiver comprising a plurality of optical fibers and photodiodes configured to detect the intensity of a specific wavelength or range of wavelengths, the particular spectral signature 802a-802d of a target gas may be identified.

Figures 8A, 8B:
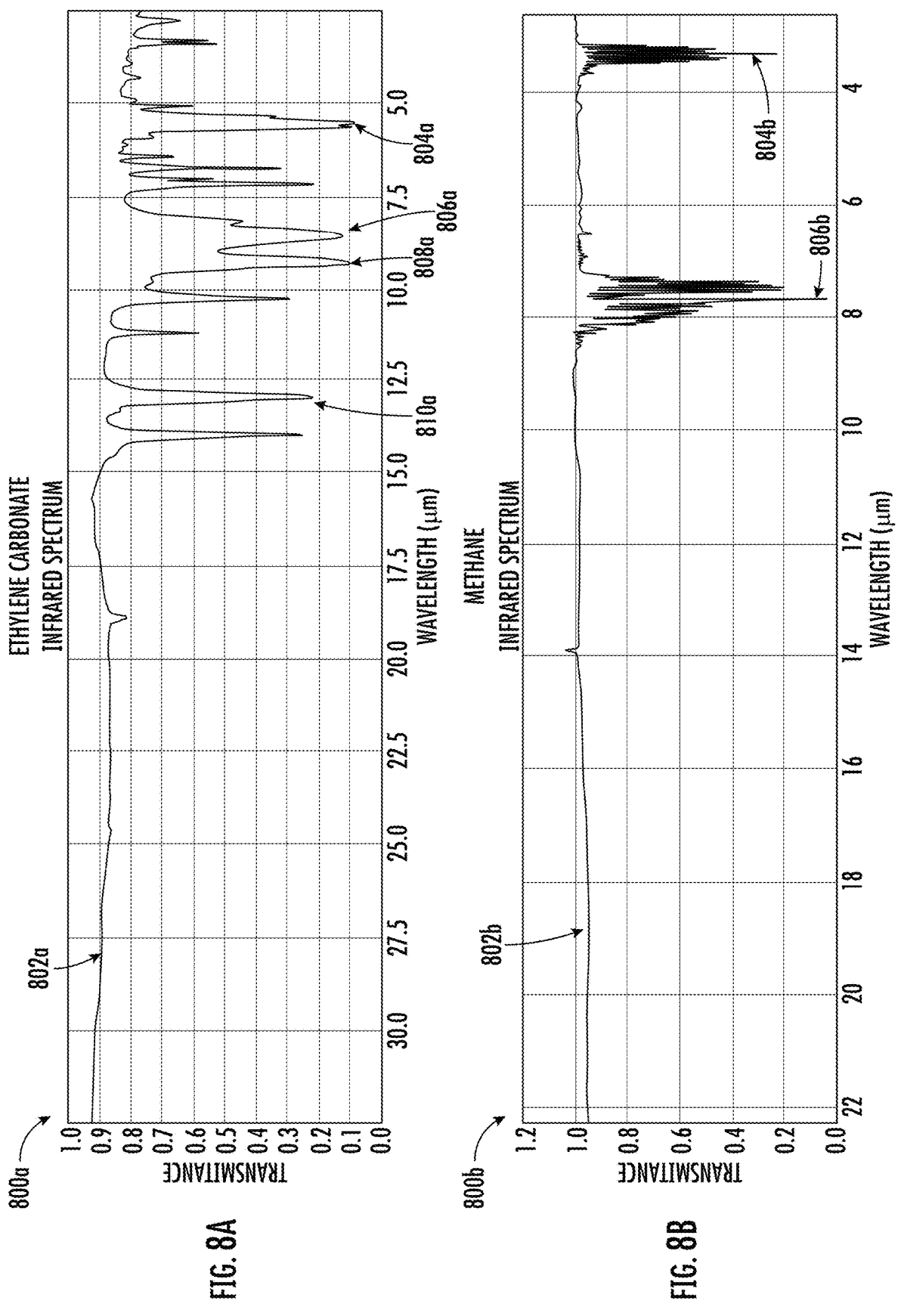
FIG. 8A-FIG. 8D depict example spectral signatures for example gases in accordance with an example embodiment of the present disclosure.

As depicted in FIG. 8A, the spectral signature 802a represents the transmittance of light across a spectrum of wavelengths in an instance in which the light passes through a gas cloud comprising ethylene carbonate. Ethylene carbonate may be a gas that is emitted from a battery cell during the first venting phase of battery decay. Detecting ethylene carbonate at an early stage may enable the use of mitigating actions to prevent the further progression of battery decay and prevent thermal runaway in a battery cell.

As depicted in FIG. 8A, the spectral signature 802a may include a number of distinguishing characteristics that may be detected by a thermal runaway detection system (e.g., thermal runaway detection system 200) in accordance with one or more example embodiments herein. For example, the spectral signature 802a of ethylene carbonate, exhibits low transmittance at points 804a, 806a, 808a, and 810a. In an example embodiment, four different optical fibers may be utilized, each configured to detect a different wavelength of light, to detect the presence of ethylene carbonate. For example, a first optical fiber may include a fiber Bragg grating, or multiple fiber Bragg gratings designed to transmit only a narrow band of light at or near 5.25 micrometers (804a). A second optical fiber may include a fiber Bragg grating, or multiple fiber Bragg gratings designed to transmit only a narrow band of light at or near 8 micrometers (806a). A third optical fiber may include a fiber Bragg grating, or multiple fiber Bragg gratings designed to transmit only a narrow band of light at or near 9 micrometers (808a). And finally, a fourth optical fiber may include a fiber Bragg grating, or multiple fiber Bragg gratings designed to transmit only a narrow band of light at or near 13 micrometers (810a). A controller (e.g., controller 212) may be configured to determine when the intensity of light received for all four optical fibers through a photodiode is below a certain minimum intensity. In an instance in which all four photodiodes coupled to the terminal end of the optical fibers produce an electrical output indicating an intensity of light below a threshold intensity, the controller 212 may determine ethylene carbonate is present, and indicate the progress of battery decay toward thermal runaway.

As depicted in FIG. 8B, the spectral signature 802b represents the transmittance of light across a spectrum of wavelengths in an instance in which the light passes through a gas cloud comprising methane. Methane may be a gas that is emitted from a battery cell during the phases of battery decay leading up to thermal runaway. Detecting methane at an early stage may enable the use of mitigating actions to prevent the further progression of battery decay and prevent thermal runaway in a battery cell.

As depicted in FIG. 8B, the spectral signature 802b may include a number of distinguishing characteristics such as the low transmittance of light at or around point 804b (light having a wavelength of approximately 3 micrometers) and at or around point 806b (light having a wavelength of approximately 7.5 micrometers). An example emitted light receiver (e.g., emitted light receiver 100) configured to detect methane, may comprise two different optical fibers, each configured to detect a different wavelength of light, to detect the presence of methane. For example, a first optical fiber may include a fiber Bragg grating, or multiple fiber Bragg gratings designed to transmit only a narrow band of light at or near 3 micrometers (804b). A second optical fiber may include a fiber Bragg grating, or multiple fiber Bragg gratings designed to transmit only a narrow band of light at or near 7.5 micrometers (806b). A controller (e.g., controller 212) may be configured to determine when the intensity of light transmitted to the photodiodes coupled to the optical fibers are both below a certain minimum intensity, indicating the presence of methane.

Figures 8C, 8D:
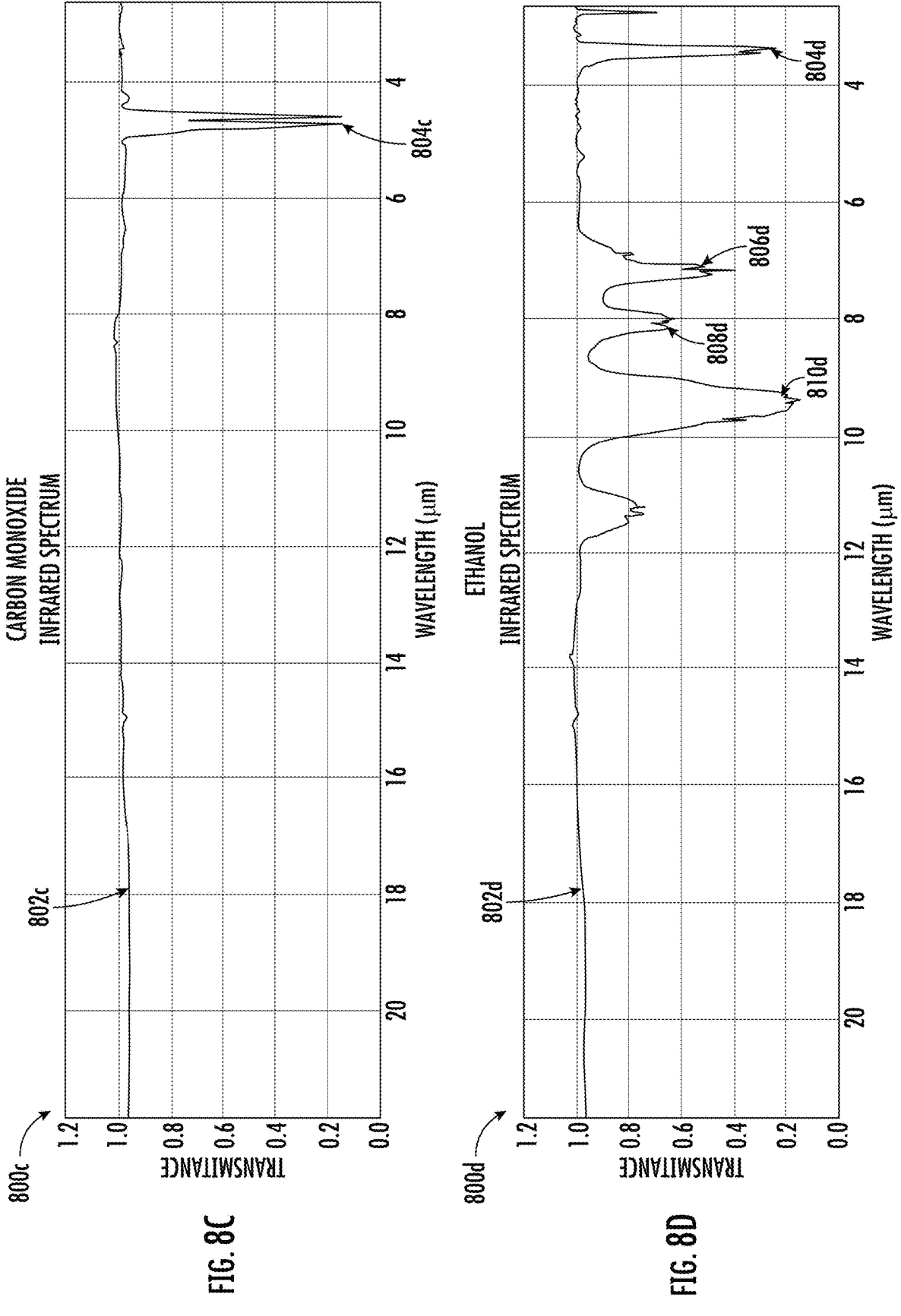

As depicted in FIG. 8C, the spectral signature 802c represents the transmittance of light across a spectrum of wavelengths in an instance in which the light passes through a gas cloud carbon monoxide. Carbon monoxide may be a gas that is emitted from a battery cell during the phases of battery decay leading up to thermal runaway. Detecting carbon monoxide at an early stage may enable the use of mitigating actions to prevent the further progression of battery decay and prevent thermal runaway in a battery cell.

As depicted in FIG. 8C, the spectral signature 802c may include a low transmittance of light at or around point 804c (light having a wavelength of approximately 4.75 micrometers). An example thermal runaway detection system (e.g., thermal runaway detection system 200) may be configured to detect such an anomaly in the received spectral signature both by recognizing the absence of light at wavelengths at or near 4.75 micrometers and by detecting the presence of light at other wavelengths.

As depicted in FIG. 8C, the spectral signature 802c represents the transmittance of light across a spectrum of wavelengths in an instance in which the light passes through a gas cloud carbon monoxide. Carbon monoxide may be a gas that is emitted from a battery cell during the phases of battery decay leading up to thermal runaway. Detecting carbon monoxide at an early stage may enable the use of mitigating actions to prevent the further progression of battery decay and prevent thermal runaway in a battery cell.

As depicted in FIG. 8D, the spectral signature 802d may include a low transmittance of light at or around points 804d (light having a wavelength of approximately 3.5 micrometers), 806d (light having a wavelength of approximately 7.25 micrometers), 808d (light having a wavelength of approximately 8 micrometers), and 810d (light having a wavelength of approximately 9.5 micrometers). An example thermal runaway detection system (e.g., thermal runaway detection system 200) may be configured to detect the relative transmittance at each of the points of interest (804*d*, 806*d*, 808*d*, and 810*d*) by configuring an optical fiber with a fiber Bragg grating allowing a narrow band of light to be transmitted through the optical fiber, the narrow band of light associated with the wavelength of the points of interest. The measured intensity of the light received may be compared with the intensity of the transmitted light and the transmittance determined. Utilizing such a mechanism may enable a gas such as ethanol to be detected in the early stages of battery decay, such that mitigating actions may be taken to prevent the further progression of battery decay and prevent thermal runaway in a battery cell.

Referring now to FIG. 9, a flowchart 900 illustrating an example method for detecting thermal runaway in a battery cell is provided.

At block 902, a controller (e.g., controller 212) may cause a light source (e.g., light source 202) to emit light (e.g., transmitted light) comprising a transmitted spectrum of wavelengths (e.g., incident light spectrum 408, 508*a*, 508*b*). The controller may manipulate the timing, intensity, wavelength, and other characteristics associated with the light source. In some embodiments, the controller may enable an array of lights (e.g., LEDs) each outputting light over a different spectrum of wavelengths emitting light over a wide band of wavelengths, for example from 0.75 micrometers to 15 micrometers. In some embodiments, the controller may configure the light source to periodically output light, for example, the controller may configure the light source to turn on once every second. The controller may additionally configure the light source to cycle through a range of wavelengths, for example, outputting light at a first wavelength for a period of time, then outputting light at a second wavelength for a period of time, and so on.

At block 904, the controller may receive, from a photodiode (e.g., receiving photodiode 106*a*-106*d*) optically coupled to a sensing fiber (e.g., optical fiber 104*a*-104*d*), an electrical output corresponding to an intensity of light received at the photodiode, wherein the sensing fiber comprises a first end (e.g., receiving end 416) and a second end (e.g., terminal end 418), wherein the sensing fiber is positioned to receive the light (e.g., received light 206) emitted by the light source at the first end, wherein the sensing fiber is optically coupled to the photodiode at the second end, and wherein the sensing fiber comprises a filtering mechanism (e.g., fiber Bragg grating 406, 506) configured to reflect a portion of the transmitted spectrum (e.g., reflected light spectrum 410, 510*a*, 510*b*) of wavelengths of the light.

In some embodiments, the controller may be electrically and/or communicatively connected to one or more photodiodes to which the optical fibers of the emitted light receiver are optically coupled. The controller may receive an analog and/or digital electrical output associated with each of the photodiodes, indicating the intensity of the light received at the photodiode. Each photodiode may be optically connected with an optical fiber comprising a filtering mechanism such as a fiber Bragg filter. The filtering mechanism may allow only certain wavelengths to be transmitted through the optical fiber, such that only the transmitted wavelengths of light passing through the filtering mechanism are received at the optically coupled photodiode. In some embodiments, a plurality of filtering mechanisms, such as fiber Bragg filters described herein, may be disposed in series along the optical fiber. In some embodiments, the filtering mechanism may be configured such that only a narrow range of wavelengths of light are transmitted through the optical fiber.

At block 906, the controller may identify a gas (e.g., gas cloud 210) based on the electrical output of the photodiode. The controller may analyze the received electrical output from the one or more photodiodes and utilized the received information to identify a particular gas. As light passes through a gas, many gases reflect, refract, and/or absorb certain wavelengths of light. As such, a gas may have an identifiable spectral signature, such as those shown in FIG. 8A-FIG. 8D. A controller may be configured to identify a gas based on the spectral signature of that gas. In some embodiments, the controller may be configured to identify certain key points of the spectral signature, such as points of a maximum or minimum transmittance. The optical fibers may be configured to transmit light having wavelengths associated with the key points of the spectral signature to the photodiodes. By comparing the received intensity of light with the transmitted intensity of the light of the same wavelength, the controller may determine the transmittance of the light for a certain wavelength. Once the transmittance of light for one or more wavelengths is determined, the controller may compare the transmittance values with the known spectral signature of a target gas. In some embodiments, other characteristics of the light, such as intensity, phase, delay, or other similar characteristics may be used to identify the gas.

In some embodiments, the controller may comprise a machine learning model defining parameters, hyper-parameters, and/or operations embedding certain characteristics of the electrical output of the one or more photodiodes to identify a gas. In such an embodiment, the controller may utilize a machine learning algorithm, such as a reinforcement learning algorithm, an unsupervised learning algorithm, and/or a supervised learning algorithm to identify a gas. Utilizing a machine learning model and algorithm, may enable a controller to consider a wider variety of characteristics of the light received at the photodiodes, such as the transmittance, the intensity, the phase, and/or how any of these characteristics change over time. A machine learning model may also enable a controller to create, correct, or update the spectral signature of one or more target gases.

At block 908, the controller may detect thermal runaway in the battery cell (e.g., battery cell 208) based at least in part on identifying the gas. A number of gases may be present at or near a decaying battery cell progressing toward thermal runaway, for example, at first venting, gases such as ethylene carbonate (EC), diethyl carbonate (DEC), dimethyl carbonate (DMC), and ethyl methyl carbonate (EMC) may be released from the battery cell. Identifying the spectral signature of one or more of these gases may be an indicator that the battery cell is decaying and approaching thermal runaway.

In some embodiments, other physical environment information related to the physical characteristics of the environment surrounding the battery cell may be gathered, for example, via sensing devices. Physical environment information may include temperature, pressure, vibrations, humidity, sounds, or other physical characteristics of the surrounding environment. In some embodiments, the physical environment information may be utilized to further determine whether a battery cell is progressing toward thermal runaway. In some embodiments, the physical environment information may be utilized to adjust and/or interpret the readings received by the controller from the one or more photodiodes. For example, some characteristics of the physical environment, such as humidity, may alter the characteristics of the fiber Bragg grating. In some embodiments, the controller may further utilize machine learning techniques to compensate for changes in the physical environment, such as humidity, pressure and temperature, when identifying gases and determining the onset of thermal runaway.

In some embodiments, mitigating actions may be taken once a controller has identified a gas indicative of battery cell decay to prevent the battery cell from further decaying and entering into thermal runaway. For example, power may be disabled to the battery cell in decay. Further, in some embodiments, visual, audio, and/or signals may be issued warning of the decay of the battery cell and the likely onset of thermal runway.

Many modifications and other embodiments of the inventions set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. The disclosed embodiments relate primarily to detecting gases related to the onset of thermal runaway, however, one skilled in the art may recognize that such principles may be applied to detecting any gas having an identifiable spectral signature. Alternative embodiments that result from combining, integrating, and/or omitting features of the embodiment(s) are also within the scope of the disclosure. Accordingly, the scope of protection is not limited by the description set out above.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure.

Use of broader terms such as "comprises," "includes," and "having" should be understood to provide support for narrower terms such as "consisting of," "consisting essentially of," and "comprised substantially of" Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

What is claimed is:

1. A system for detecting a gas, the system comprising:
a light source configured to emit light comprising a spectrum of wavelengths; and
a sensing fiber comprising a first end and a second end,
   wherein the sensing fiber is positioned to receive the light emitted by the light source at the first end,
   wherein the sensing fiber is optically coupled to a photodiode at the second end, and
   wherein the sensing fiber comprises a filtering mechanism configured to reflect a portion of the spectrum of wavelengths of the light, wherein another portion of the spectrum of wavelengths of the light is received by the photodiode through the sensing fiber;
wherein the gas is detected based on comparing the spectrum of wavelengths of the light received by the photodiode, determined from an electrical output of the photodiode, with a spectral signature of the gas, and wherein detection is based on comparing the spectrum of wavelengths of the light received by the photodiode with a stored spectral signature of the gas, and requires that at least two electrical outputs meet respective threshold conditions indicative of the gas.

2. The system of claim 1, wherein the filtering mechanism is a fiber Bragg grating configured to reflect a reflected wavelength of the spectrum of wavelengths.

3. The system of claim 2, wherein the sensing fiber comprises a plurality of filtering mechanisms wherein each of the plurality of filtering mechanisms is configured to reflect a different portion of the spectrum of wavelengths.

4. The system of claim 1, further comprising a plurality of sensing fibers each sensing fiber optically coupled to a receiving photodiode, wherein the filtering mechanism of each of the plurality of sensing fibers is configured to reflect a different portion of the spectrum of wavelengths.

5. The system of claim 4, wherein the gas impedes a transmittance of the light within the transmitted spectrum of wavelengths according to a spectral signature, and wherein the plurality of sensing fibers are configured to identify the gas according to the spectral signature of the gas.

6. The system of claim 1, wherein the light source comprises an array of light emitting diodes.

7. The system of claim 1, wherein the spectrum of wavelengths comprises light of wavelengths between 0.75 micrometers and 15 micrometers.

8. The system of claim 1, wherein the gas comprises at least one of ethylene carbonate, diethyl carbonate, dimethyl carbonate, and ethyl methyl carbonate.

9. The system of claim 1, further comprising a battery cell, wherein the light source and sensing fiber are positioned proximate the battery cell.

10. The system of claim 9, wherein detecting the gas is an indicator of a first venting previous to an onset of thermal runaway in the battery cell.

11. The system of claim 1, further comprising a processor electrically connected to the light source and the photodiode, wherein the processor is configured to determine a presence of the gas based on an electrical output of the photodiode.

12. The system of claim 11, wherein the processor utilizes machine learning techniques to detect the gas based on the output of the photodiode.

13. The system of claim 11, wherein the processor further receives physical environment information from one or more sensing devices and alters at least one detection parameter based on the physical environment information.

14. A method for detecting thermal runaway in a battery cell, the method comprising:

causing a light source to emit light comprising a transmitted spectrum of wavelengths;

receiving, from a photodiode optically coupled to a sensing fiber, an electrical output corresponding to an intensity of light received at the photodiode, wherein the sensing fiber comprises a first end and a second end, wherein the sensing fiber is positioned to receive the light emitted by the light source at the first end, wherein the sensing fiber is optically coupled to the photodiode at the second end, and wherein the sensing fiber comprises a filtering mechanism configured to reflect a portion of the transmitted spectrum of wavelengths of the light, wherein another portion of the spectrum of wavelengths of the light is received by the photodiode through the sensing fiber;

identifying a gas based on the electrical output of the photodiode; and detecting thermal runaway in the battery cell based at least in part on identifying the gas, wherein the gas is detected based on comparing the spectrum of wavelengths of the light received by the photodiode, determined from an electrical output of the photodiode, with a spectral signature of the gas, and wherein detection is based on comparing the spectrum of wavelengths received by the photodiode with a stored spectral signature of the gas, and requires that at least two electrical outputs meet respective threshold conditions indicative of the gas.

15. The method of claim 14, further comprising utilizing machine learning techniques to identify the gas based on the electrical output of the photodiode.

16. The method of claim 14, further comprising utilizing a plurality of sensing fibers each sensing fiber optically coupled to a receiving photodiode to detect the gas, wherein the filtering mechanism of each of the plurality of sensing fibers is configured to reflect a different portion of the transmitted spectrum of wavelengths.

17. The method of claim 16, wherein the gas impedes a transmittance of the light within the transmitted spectrum of wavelengths according to a spectral signature, and wherein the plurality of sensing fibers are configured to identify the gas according to the spectral signature of the gas.

18. The method of claim 14, further comprising:

receiving physical environment information from one or more sensing devices; and altering at least one detection parameter based on the physical environment information.

19. The method of claim 14, wherein the transmitted spectrum of wavelengths comprises light of wavelengths between 0.75 micrometers and 15 micrometers.

20. A computer program product for detecting thermal runaway in a battery cell, the computer program product comprising at least one non-transitory computer-readable storage medium having computer-readable program code portions stored therein, the computer-readable program code portions comprising an executable portion configured to:

cause a light source to emit light comprising a transmitted spectrum of wavelengths;

receive, from a photodiode optically coupled to a sensing fiber, an electrical output corresponding to an intensity of light received at the photodiode, wherein the sensing fiber comprises a first end and a second end, wherein the sensing fiber is positioned to receive the light emitted by the light source at the first end, wherein the sensing fiber is optically coupled to the photodiode at the second end, and wherein the sensing fiber comprises a filtering mechanism configured to reflect a portion of the transmitted spectrum of wavelengths of the light, wherein another portion of the spectrum of wavelengths of the light is received by the photodiode through the sensing fiber;

identify a gas based on the electrical output of the photodiode; and detect thermal runaway in the battery cell based at least in part on identifying the gas, wherein the gas is detected based on comparing the spectrum of wavelengths of the light received by the photodiode, determined from an electrical output of the photodiode, with a spectral signature of the gas, and wherein detection is based on comparing the spectrum of wavelengths received by the photodiode with a stored spectral signature of the gas, and requires that at least two electrical outputs meet respective threshold conditions indicative of the gas.

* * * * *